US010494427B2

(12) United States Patent
Delcros et al.

(10) Patent No.: US 10,494,427 B2
(45) Date of Patent: Dec. 3, 2019

(54) ANTI-NETRIN-1 ANTIBODY

(71) Applicant: NETRIS PHARMA, Lyons (FR)

(72) Inventors: Jean-Guy Delcros, Lyons (FR); Yann Dean, Bossey (FR)

(73) Assignee: NETRIS PHARMA, Lyons (FR)

( * ) Notice: Subject to any disclaimer, the term of this patent is extended or adjusted under 35 U.S.C. 154(b) by 95 days.

(21) Appl. No.: 15/110,612

(22) PCT Filed: Jan. 9, 2015

(86) PCT No.: PCT/EP2015/050306

§ 371 (c)(1),
(2) Date: Jul. 8, 2016

(87) PCT Pub. No.: WO2015/104360

PCT Pub. Date: Jul. 16, 2015

(65) Prior Publication Data

US 2018/0072800 A1 Mar. 15, 2018

(30) Foreign Application Priority Data

Jan. 10, 2014 (EP) .................................... 14305034

(51) Int. Cl.

*C07K 16/18* (2006.01)
*A61K 39/395* (2006.01)
*C07K 16/22* (2006.01)
*A61K 39/00* (2006.01)

(52) U.S. Cl.

CPC ............ *C07K 16/22* (2013.01); *A61K 39/395* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search

None
See application file for complete search history.

(56) References Cited

U.S. PATENT DOCUMENTS 7,456,151 B2 11/2008 Li et al.
8,097,253 B2 1/2012 Li et al.
2006/0019896 A1 1/2006 Li et al.
2006/0153840 A1 7/2006 Eichmann et al.
2009/0226458 A1 9/2009 Mehlen et al.
2010/0040622 A1 2/2010 Li et al.
2010/0183520 A1* 7/2010 Ramesh ............... C12Q 1/6883 424/9.2
2012/0015364 A1 1/2012 Mehlen et al.
2015/0004159 A1 1/2015 Mehlen et al.
2018/0291106 A1 10/2018 Mehlen et al.

FOREIGN PATENT DOCUMENTS

EP 2208738 7/2010
FR 2 878 165 5/2006
WO WO-0233080 4/2002
WO WO-2005-074556 8/2005
WO WO-2006-019904 2/2006
WO WO-2006-054000 5/2006
WO WO-2009-141440 11/2009
WO WO-2010-059821 5/2010
WO WO-2012-025618 3/2012
WO WO-2014-041078 3/2014
WO WO-2014-041088 3/2014

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Portolano (The Journal of Immunology, vol. 150, No. 3, p. 880-887, 1993) (Year: 1993).*
Beiboer (J. Mol. Biol. (2000) 296:833-849) (Year: 2000).*
Johnson and Wu (Methods in Molecular Biology, Antibody Engineering: Methods and Protocols, vol. 248, p. 11-25, 2004) (Year: 2004).*
Rudikoff et al. (Proc Natl Acad Sci USA 79: 1979-1983, 1982) (Year: 1982).*
Polyak et Al. (Blood, vol. 99, No. 9, p. 3256-3262, 2002) (Year: 2002).*
Munodzana et Al. (Infection and Immunity, vol. 66 No. 6, p. 2619-2624, 1998) (Year: 1998).*
International Search Report dated Mar. 20, 2015 in International Application No. PCT/EP2015/050306.
Won Park, et al., The axonal attractant Netrin-1 is an angiogenic factor PNAS 2004 101 (46) 16210-16215; published ahead of print Nov. 1, 2004, doi:10.1073/pnas.0405984101.
Yang et al., "Autoproteolytic Activation of Pro-Caspases by Oligomerization", Jan. 1998, vol. 1, Issue 2 , 319-325.
Yebra et al., "Recognition of the Neural Chemoattractant Netrin-1 by Integrins α6β4 and α3β1 Regulates Epithelial Cell Adhesion and Migration", Nov. 2003, 695-707, Developmental Cell—vol. 5.
Wang, et al., "Dimerization-dependent block of the proapoptotic effect of P75NTR", 2000, 587-593, vol. 50—Issue 5, Journal of Neuroscience Research.

(Continued)

*Primary Examiner* — Michael Allen
(74) *Attorney, Agent, or Firm* — B. Aaron Schulman, Esq.; Sites & Harbison, PLLC

(57) ABSTRACT

The application discloses a linear or substantially linear epitope on netrin-1 that likely corresponds to the specific binding region of netrin-1 to receptor, in particular of the UNC5 class, especially UNC5B and UNC5A, or alternatively corresponds to a region nearby the specific binding region of netrin-1 to receptor that when bound to an antibody prevents netrin-1/receptor interaction. This determination of a linear epitope allows the Applicant to produce antibodies binding to netrin-1 and interfering with netrin-1/receptor interaction, thereby inducing apoptosis or cell death of tumour cells expressing or overexpressing netrin-1 and at least one netrin-1 receptor, owing the fact that this interaction inhibits netrin-1 binding to a receptor and the multimerization of the receptor. The application discloses a murine monoclonal antibody directed against this epitope and various humanized forms thereof.

14 Claims, 6 Drawing Sheets

Specification includes a Sequence Listing.

(56) References Cited

OTHER PUBLICATIONS

B. D. Wilson, et al., "Netrins Promote Developmental and Therapeutic Angiogenesis", 2006, pp. 640-644, *Science*, vol. 313—Issue 5787, Web.
Thibert, et al., "Inhibition of Neuroepithelial Patched-Induced Apoptosis by Sonic Hedgehog", Aug. 8, 2003, *Science*, vol. 301—Issue 5634, Web.
Thiébault, et al., "The Netrin-1 Receptors UNC5H Are Putative Tumor Suppressors Controlling Cell Death Commitment", Apr. 1, 2003, pp. 4173-4178, vol. 100—No. 7, published ahead of print Mar. 24, 2003, doi:10.1073/pnas.0738063100.
Stupack, et al., "Apoptosis of Adherent Cells by Recruitment of Caspase-8 to Unligated Integrins", 2001, pp. 459-470, *J Cell Biol the Journal of Cell Biology*, vol. 155—Issue 3, Web.
Stupack, et al., "Potentiation of neuroblastoma metastasis by loss of caspase-8", Jan. 2006, pp. 95-99, vol. 439—Issue 5, doi:10.1038/nature04323.
Tanikawa, et al., "p53RDL1 Regulates p53-dependent Apoptosis", Feb. 2003, pp. 216-223, vol. 5, doi: 10.1038/ncb943.
Yebra, et al, "Recognition of the Neural Chemoattractant Netrin-1 by Integrins a6β4 and α3β1 Regulates Epithelial Cell Adhesion and Migration", Nov. 2003, pp. 695-707, vol. 5, Developmental Cell.
Srinivasan, et al., "Netrin-1/Neogenin Interaction Stabilizes Multipotent Progenitor Cap Cells during Mammary Gland Morphogenesis", Mar. 2003, pp. 371-382, vol. 4, Developmental Cell.
Serafini, et al., "Netrin-1 is Required for Commissural Axon Guidance in the Developing Vertebrate Nervous System", Dec. 13, 1996, pp. 1001-1014, vol. 87, Cell.
Stein, et al., Binding of DCC by Netrin-1 to Mediate Axon Guidance Independent of Adenosine A2B Receptor Activation, Mar. 9, 2001, pp. 1976-1982, vol. 291, Science.
Paradisi, et al., "Netrin-1 up-regulation in inflammatory bowel diseases is required for colorectal cancer progression", 2009, pp. 1-6, PNAS Early Edition.
Rabizadeh, et al., "Induction of Apoptosis by the Low-Affinity NGF Receptor", Jul. 16, 1993, pp. 345-348, vol. 261, Science.
Serafini, et al., The Netrins Define a Family of Axon Outgrowth-Promoting Proteins Momologous to C. elegans UNC-6, Aug. 12, 1994, pp. 409-424, vol. 78, Cell.
Muppidi, et al, "Life and Death Decisions: Secondary Complexes and Lipid Rafts in TNF Receptor Family Signal Transduction", Oct. 2004, pp. 461-465, vol. 21, Immunity.
Nguyen, et al., "Netrin-1 induces angiogenesis via a DCC-dependent ERK1/2-eNOS feed-forward mechanism", Apr. 25, 2006, pp. 6530-6535, vol. 103, No. 17, PNAS.
Bernet, et al., "Netrin-1 and its dependence receptors: role in colorectal cancers", 2005, pp. 328-333, vol. 53, Pathologie Biologie.
Ackerman, et al., "The mouse rostral cerebellar malformation gene encodes an UNC-5-like protein", Apr. 24, 1997, pp. 838-842, vol. 386, Nature.
Bernet, et al., "Inactivation of the UNC5C Netrin-1 Receptor Is Associated with Tumor Progression in Colorectal Malignancies", 2007, pp. 1840-1848, vol. 133, Gastroenterology.
Andre, et al., "Breast Center with Synchronous Metastases: Trends in Survival During a 14-year Period", Aug. 15, 2004, vol. 22, No. 16, pp. 3302-3308, Journal of Clinical Oncology.
Aslakson, et al., "Selective Events in the Metastatic Process Defined by Analysis of the Sequential Dissemination of Subpopulations of a Mouse Mammary Tumor", Mar. 15, 1992, pp. 1389-1405, vol. 52, Cancer Research.
Bredesen, et al., "Receptors that mediate cellular dependence", 2005, pp. 1031-1043, vol. 12, Cell Death and Differentiation.
Chan, et al., "UNC-40, a C. elegans Homolog of DCC (Deleted in Colorectal Cancer), is Required in Motile Cells Responding to UNC-6 Netrin Cues", Oct. 18, 1996, pp. 187-195, vol. 87, Cell.
Bordeaux, et al., "The RET proto-oncogene induces apoptosis: a novel mechanism for Hirschsprung disease", 2000, pp. 4056-4063, vol. 19, No. 15, The EMBO Journal.
De Kok, et al., "Normalization of gene expression measurements in tumor tissues: comparison of 13 endogenous control genes", 2005, pp. 154-159, vol. 85, Laboratory Investigation.
De Cremoux, et al., "Inter-laboratory quality control for hormone-dependent gene expression in human breast tumors using real-time reverse transcription-polymerase chain reaction", 2004, pp. 489-495, vol. 11, Endocrine-Related Cancer.
Ellerby, et al., "Kennedy's Disease Caspase Cleavage of the Androgen Receptor is a Crucial Event in Cytotoxicity", 1999, pp. 185-195, vol. 72, No. 1, J. Neurochem.
Fearon, et al., "Identification of a Chromosome 18q Gene That is Altered in Colorectal Cancers", Jan. 5, 1990, pp. 49-56, vol. 247, Science.
Delloye-Bourgeois, et al., Interference With Netrin-1 and Tumor Cell Death in Non-Small Cell Lung Cancer, Feb. 18, 2009, pp. 237-247, vol. 101, No. 4, JNCI: Articles.
Forcet, et al., "The dependence receptor DCC (deleted in colorectal cancer) defines an alternative mechanism for caspase activation", Mar. 13, 2001, pp. 3416-3421, vol. 98, no. 6, PNAS.
Fitamant, et al., "Netrin-1 expression confers a selective advantage for tumor cell survival in metastatic breast cancer", Mar. 25, 2008, pp. 4850-4855, vol. 105, No. 12, PNAS.
Fazeli, et al., "Phenotype of mice lacking functional *Deleted in colorectal cancer* (*Dcc*) gene", Apr. 24, 1997, pp. 796-804, vol. 386, Nature.
Hedgecock, et al., "The unc-5, unc-6, and unc-40 Genes Guide Circumferential Migrations of Pioneer Axons and Mesodermal Cells on the Epidermis in C. elegans", Jan. 1990, pp. 61-85, vol. 2, Neuron.
Kruger, et al., "Mapping Netrin Receptor Binding Reveals Domains of Unc5 Regulating Its Tyrosine Phosphorylation", Dec. 1, 2004, pp. 10826-10834, vol. 24, No. 48, The Journal of Neuroscience.
Mehlen, et al., "Netrin-1: when a neuronal guidance cue turns out to be a regulator of tumorigenesis", 2005, pp. 1-18, CMLS, Cell. Mol. Life Sci.
Keino-Masu, et al., "Deleted in Colorectal Cancer (DCC) Encodes a Netrin Receptor", Oct. 16, 1996, pp. 175-185, vol. 87, Cell.
Geisbrecht, et al., Netrin Binds Discrete Subdomains of DCC and UNC5 and Mediates Interactions between DCC and Heparin, Aug. 29, 2009, pp. 32561-32568, vol. 278, No. 35, The Journal of Biological Chemistry.
Inbal, et al., "DAP kinase links the control of apoptosis to metastasis", Nov. 13, 1997, pp. 180- 184, vol. 390, Nature.
Forcet, et al., "Netrin-1-mediated axon outgrowth requires deleted in colorectal cancer-dependent MAPK activation", May 23, 2002, pp. 443-447, vol. 417, Nature.
Hong, et al, "A Ligand-Gated Association between Cytoplasmic Domains of UNC5 and DCC Family Receptors Converts Netrin-Induced Growth Cone Attraction to Repulsion", Jun. 25, 1999, pp. 927-941, vol. 97, Cell.
Llambi, et al., "The dependence receptor UNC5H2 mediates apoptosis through DAP-kinase", 2005, pp. 1-10, The EMBO Journal.
Llambi, et al, "Netrin-1 acts as a survival factor via its receptors UNC5H and DCC", 2001, pp. 2715-2722, vol. 20, No. 11, The EMBO Journal.
Kinzler, et al., "Lessons from Hereditary Colorectal Cancer", Oct. 18, 1996, pp. 159-170, vol. 87, Cell.
Latil, et al, "Quantification of Expression of Netrins, Slits and Their Receptors in Human Prostate Tumors", 2003, pp. 306-315, vol. 103, Int. J. Cancer.
Liu, et al., "Novel Role for Netrins in Regulating Epithelial Behavior during Lung Branching Morphogenesis", May 25, 2064, pp. 897-905, vol. 14, Current Biology.
Mehlen, et al, "The dependence receptor hypothesis", 2004, pp. 37-49, vol. 9, Apoptosis.
Mehlen, et al, "Role of the Dependence Receptor DCC in Colorectal Cancer Pathogenesis", Aug. 15, 2004, pp. 3420-3428, vol. 22, No. 16, Journal of Clinical Oncology.
Lu, et al, "The netrin receptor UNC5B mediates guidance events controlling morphogenesis of the vascular system", Nov. 11, 2004, pp. 179-186, vol. 432, Nature.

(56) References Cited

OTHER PUBLICATIONS

Mehlen, et al., The DCC gene product induces apoptosis by a mechanism requiring receptor proteolysis, Oct. 22, 199 8, pp. 801-804, vol. 395, Nature.
Lv, et al., "Genetic and epigenetic control of UNC5C expression in human renal cell carcinoma", 2011, pp. 2068-2076, vol. 47, European Journal of Cancer.
Matsunaga, et al., "RGM and its receptor neogenin regulate neuronal survival", Aug. 2004, pp. 749-755, vol. 6, No. 8, Nature Cell Biology.
Mazelin, et al., "Netrin-1 controls colorectal tumorigenesis by regulating apoptosis", Sep. 2, 2004, pp. 80-84, vol. 431, Nature.
Bernet, et al., "Inactivation of the UNC5C netrin-1 receptor is associated with tumor progression in colorectal malignancies", Dec. 2007, pp. 1840-1848, vol. 133, No. 6, Gastroenterology.
Castets, et al., "DCC constrains tumor progression via its dependence receptor activity", 2011, pp. 1-5, Nature.
Castets, et al., "Inhibition of Endothelial Cell Apoptosis by Netrin-1 during Angiogenesis", Apr. 21, 2009, pp. 614-620, vol. 16, Developmental Cell.
Braisted, et al., "Netrin-1 Promotes Thalamic Axon Growth and Is Required for Proper Development of the Thalamocortical Projection", Aug. 1, 2000, pp. 5792-5801, vol. 20, No. 15, The Journal of Neuroscience.
Broutier, et al., "Targeting netrin-1/DCC interaction in diffuse large B-cell and mantle cell lymphomas", Jan. 31, 2016, pp. 96-104, vol. 8, No. 2, EMBO Molecular Medicine.
Coissieux, et al., "Variants in the Netrin-1 Receptor UNC5C Prevent Apoptosis and Increase Risk for Familial Colorectal Cancer", Dec. 2011, pp. 2039-2046, vol. 141, No. 6, Gastroenterology.
Delloye-Bourgeois, et al., "Netrin-1 acts as a survival factor for aggressive neuroblastoma", 2009, pp. 833-847, vol. 206, No. 4, J. Exp. Med.
Delloye-Bourgeois, et al, "Nucleolar Localization of a Netrin-1 Isoform Enhances Tumor Cell Proliferation", Aug. 7, 2012, pp. 1-15, vol. 5, No. 236, Science Signaling.
Furne, et al., "The dependence receptor DCC requires lipid raft localization for cell death signaling", Mar. 14, 2006, pp. 4128,4133, vol. 103, No. 11, PNAS.
Harter, et al., "Netrin-1 Expression is an Independent Prognostic Factor for Poor Patient Survival in Brain Metastases", Mar. 2014, pp. 1-10, vol. 9, No. 3, PLoS One.
Gibert, et al., "Dependence Receptors and Cancer: Addiction to Trophic Ligands", Dec. 15, 2015, pp. 5171-5175, vol. 75, No. 24, Cancer Res.
Guenebeaud, et al., "The Dependence Receptor UNC5H2/B Triggers Apoptosis via PP2A-Mediated Dephosphorylation of DAP Kinase", Dec. 22, 2010, pp. 863-876, vol. 40, Molecular Cell.
Furne, et al., "Netrin-1 is a survival factor during commissural neuron navigation", Sep. 23, 2008, pp. 14465-14470, vol. 105, No. 38, PNAS.
Grandin, et al., "Structural Decoding of the Netrin-1/UNC5 Interaction and its Therapeutical Implications in Cancers", Feb. 8, 2016, pp. 173-185, vol. 29, Cancer Cell.
Mehlen, et al, "Role of netrin-1 and netrin-1 dependence receptors in colorectal cancer", 2005, pp. 1-6, vol. 93, No. 1, British Journal of Cancer.
Llambi, et al., "The dependence receptor UNC5H2 mediates apoptosis through DAP-kinase", 2005, pp. 1192-1201, vol. 24, The EMBO Journal.
Maisse, et al., "Lipid raft localization and palmitoylation: Identification of two requirements for cell death induction by the tumor suppressors UNC5H", 2008, pp. 2544-2552, vol. 314, Experimental Cell Research.
Luchino, et al., "Semaphorin 3E Suppresses Tumor Cell Death Triggered by Plexin D1 Dependence Receptor in Metastatic Breast Cancers", Nov. 11, 2013, pp. 673-685, vol. 24, Cancer Cell.
Lourenco, et al., "Netrin-1 interacts with amyloid precursor protein and regulates amyloid-β production", 2009, pp. 655-663, vol. 16, Cell Death and Differentiation.
Hérincs, et al., "DCC association with lipid rafts is required for netrin-1-mediated axon guidance", 2005, pp. 1687-1692, vol. 118, No. 8, Journal of Cell Science.
Zhu, et al, "Dependence receptor UNC5D mediates nerve growth factor depletion-induced neuroblastoma regression", Jul. 2013, pp. 2935-2947, vol. 123, No. 7, The Journal of Clinical Investigation.
Mehlen, et al., "Novel roles for Slits and netrins: axon guidance cues as anticancer targets?", Mar. 2011, pp. 188-197, vol. 11, Nature Reviews: Cancer.
Rama, et al., "Amyloid Precursor Protein Regulates Netrin-1-mediated Commissural Axon Outgrowth", Aug. 24, 2012, pp. 30014-30023, vol. 287, No. 35, The Journal of Biological Chemistry.
Wang, et al., "Netrin-1 Overexpression Protects Kidney from Ischemia Reperfusion Injury by Suppressing Apoptosis", Sep. 3, 2009, pp. 1010-1018, vol. 175, No. 3, The American Journal of Pathology.
Ozmadenci, et al., Netrin-1 regulates somatic cell reprogramming and pluripotency maintenance, Jul. 8, 2015, pp. 1-11, Nature Communications.
Paradisi, et al., "Combining chemotherapeutic agents and netrin-1 interference potentiates cancer cell death", 2013, pp. 1821-1834, vol. 5, EMBO Mol Med.
Rajasundari, et al., "Netrin-1 overexpression in kidney proximal tubular epithelium ameliorates cisplatin nephrotoxicity", Dec. 2011, pp. 1717-1726, vol. 91, No. 12, Lab Invest.
Mille, et al., "Interfering with multimerization of netrin-1 receptors triggers tumor cell death", 2009, pp. 1344-1351, vol. 16, Cell Death and Differentiation.
Tang, et al., "Netrin-1 Mediates Neuronal Survival Through PIKE-L Interaction with the Dependence Receptor UNC5B", Jun. 2008, pp. 698-706, vol. 10, No. 6, Nat Cell Biol.
Mehlen, et al., "Netrin-1 and its dependence receptors as original targets for cancer therapy", 2010, pp. 46-54, vol. 22, Current Opinion in Oncology.
Paradisi, et al., "Nf-κB Regulates Netrin-1 Expression and Affects the Conditional Tumor Suppressive Activity of the Netrin-1 Receptors", 2008, pp. 1248-1257, vol. 135, Gastroenterology.
Llambi, F. (2001). Netrin-1 acts a survival factor vua its receptors UNC5H and DCC. *The EMBO Journal*, 20(11), 2715-2722. doi:10-1093/emboj/20.11.2715.
Lv, D., Zhao, W., Dong, D., Qian, X., Zhang, Y., Tian, X., & Zhang, J. (2011). Genetic and epigenetic control of UNC5C expression in human renal cell carcinoma. *European Journal of Cancer*, 47(13), 2068-2076. doi:10.1016/j.ejca.2011.04.021.
Mehlen, P., Rabizadeh, S., Snipas, S. J., Assa-Munt, N., Salvesen, G. S., & Bredesen, D. E. (1998). The DCC gene product induces apoptosis by a mechanism requiring receptor proteolysis. *Nature*, 395(6704), 801-804. doi:10.1038/27441.
Ozmadenci, D., Féraud, O., Markossian, S., Kress, E., Ducarouge, B., Gibert, B., Lavial. F. (2015). Netrin-1 regulates somatic cell reprogramming and pluripotency maintenance. *Nature Communications*, 6(1), 1-11. doi:10.1038/ncomms8398.
Rabizadeh. S., Oh, J., Zhong, L., Yang. J., Bitler, C., Butcher, L., & Bredesen, D. (1993). Induction of apoptosis by the low-affinity NGF receptor. *Science*, 261(5119), 345-348. doi:10.1126/science.8332899.
Stein, E. (2001). Binding of DCC by Netrin-1 to Mediate Axon Guidance Independent of Adenosine A2B Receptor Activation. *Science*, 291(5510), 1976-1982. doi:10.1126/science.1059391.
Serafini, T., Kennedy, T. E., Gaiko, M. J., Mirzayan, C., Jessell, T. M., & Tessier-Lavigne, M. (1994). The netrins define a family of axon outgrowth-promoting proteins homologous to C. elegans UNC-6. *Cell*,78(3), 409-424. doi:10.1016/0092-8674(94)90420-0.
Geisbrecht, B. V., Dowd, K. A., Barfield, R. W., Longo, P. A., & Leahy, D. J. (2003). Netrin Binds Discrete Subdomains of DCC and UNC5 and Mediates Interactions between DCC and Heparin. *Journal of Biological Chemistry*, 278(35), 32561-32568. doi:10.1074/jbc.m302943200.

* cited by examiner

SEQUENCE LISTING

```
<160> NUMBER OF SEQ ID NOS: 36

<210> SEQ ID NO 1
<211> LENGTH: 604
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: MISC_FEATURE
<222> LOCATION: (339)..(381)
<223> OTHER INFORMATION: linear epitope

<400> SEQUENCE: 1

Met Met Arg Ala Val Trp Glu Ala Leu Ala Ala Leu Ala Ala Val Ala
1               5                   10                  15

Cys Leu Val Gly Ala Val Arg Gly Gly Pro Gly Leu Ser Met Phe Ala
            20                  25                  30

Gly Gln Ala Ala Gln Pro Asp Pro Cys Ser Asp Glu Asn Gly His Pro
        35                  40                  45

Arg Arg Cys Ile Pro Asp Phe Val Asn Ala Ala Phe Gly Lys Asp Val
    50                  55                  60

Arg Val Ser Ser Thr Cys Gly Arg Pro Pro Ala Arg Tyr Cys Val Val
65                  70                  75                  80

Ser Glu Arg Gly Glu Glu Arg Leu Arg Ser Cys His Leu Cys Asn Ala
                85                  90                  95
```

```
Ser Asp Pro Lys Lys Ala His Pro Pro Ala Phe Leu Thr Asp Leu Asn
            100                 105                 110

Asn Pro His Asn Leu Thr Cys Trp Gln Ser Glu Asn Tyr Leu Gln Phe
        115                 120                 125

Pro His Asn Val Thr Leu Thr Leu Ser Leu Gly Lys Lys Phe Glu Val
    130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
                165                 170                 175

Tyr Ser Thr Gln Cys Arg Lys Met Tyr Asn Arg Pro His Arg Ala Pro
            180                 185                 190

Ile Thr Lys Gln Asn Glu Gln Glu Ala Val Cys Thr Asp Ser His Thr
        195                 200                 205

Asp Met Arg Pro Leu Ser Gly Gly Leu Ile Ala Phe Ser Thr Leu Asp
    210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255

Phe Gly Asp Glu Asn Glu Asp Asp Ser Glu Leu Ala Arg Asp Ser Tyr
            260                 265                 270

Phe Tyr Ala Val Ser Asp Leu Gln Val Gly Gly Arg Cys Lys Cys Asn
        275                 280                 285

Gly His Ala Ala Arg Cys Val Arg Asp Arg Asp Asp Ser Leu Val Cys
    290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
            340                 345                 350

Asn Met Glu Leu Tyr Lys Leu Ser Gly Arg Lys Ser Gly Gly Val Cys
        355                 360                 365

Leu Asn Cys Arg His Asn Thr Ala Gly Arg His Cys His Tyr Cys Lys
    370                 375                 380

Glu Gly Tyr Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
            420                 425                 430

Thr Cys Asn Arg Cys Ala Lys Gly Tyr Gln Gln Ser Arg Ser Pro Ile
        435                 440                 445

Ala Pro Cys Ile Lys Ile Pro Val Ala Pro Pro Thr Thr Ala Ala Ser
    450                 455                 460

Ser Val Glu Glu Pro Glu Asp Cys Asp Ser Tyr Cys Lys Ala Ser Lys
465                 470                 475                 480

Gly Lys Leu Lys Ile Asn Met Lys Lys Tyr Cys Lys Lys Asp Tyr Ala
                485                 490                 495

Val Gln Ile His Ile Leu Lys Ala Asp Lys Ala Gly Asp Trp Trp Lys
            500                 505                 510
```

```
Phe Thr Val Asn Ile Ile Ser Val Tyr Lys Gln Gly Thr Ser Arg Ile
        515                 520                 525

Arg Arg Gly Asp Gln Ser Leu Trp Ile Arg Ser Arg Asp Ile Ala Cys
    530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
            580                 585                 590

Gln Gln Arg Glu Lys Lys Gly Lys Cys Lys Lys Ala
        595                 600
```

<210> SEQ ID NO 2
<211> LENGTH: 1817
<212> TYPE: DNA
<213> ORGANISM: Homo sapiens

<400> SEQUENCE: 2

```
atgatgcgcg cagtgtggga ggcgctggcg gcgctggcgg cggtggcgtg cctggtgggc      60

gcggtgcgcg gcgggcccgg gctcagcatg ttcgcgggcc aggcggcgca gcccgatccc     120

tgctcggacg agaacggcca cccgcgccgc tgcatcccgg actttgtcaa tgcggccttc     180

ggcaaggacg tgcgcgtgtc cagcacctgc ggccggcccc cggcgcgcta ctgcgtggtg     240

agcgagcgcg gcgaggagcg gctgcgctcg tgccacctct gcaacgcgtc cgaccccaag     300

aaggcgcacc cgcccgcctt cctcaccgac ctcaacaacc cgcacaacct gacgtgctgg     360

cagtccgaga actacctgca gttcccgcac aacgtcacgc tcacactgtc cctcggcaag     420

aagttcgaag tgacctacgt gagcctgcag ttctgctcgc cgcggcccga gtccatggcc     480

atctacaagt ccatggacta cgggcgcacg tgggtgccct tccagttcta ctccacgcag     540

tgccgcaaga tgtacaaccg gccgcaccgc gcgcccatca ccaagcagaa cgagcaggag     600

gccgtgtgca ccgactcgca caccgacatg cgcccgctct cgggcggcct catcgccttc     660

agcacgctgg acgggcggcc ctcggcgcac gacttcgaca actcgcccgt gctgcaggac     720

tgggtcacgg ccacagacat ccgcgtggcc ttcagccgcc tgcacacgtt cggcgacgag     780

aacgaggacg actcggagct ggcgcgcgac tcgtacttct acgcggtgtc cgacctgcag     840

gtgggcggcc ggtgcaagtg caacggccac gcggcccgct gcgtgcgcga ccgcgacgac     900

agcctggtgt gcgactgcag gcacaacacg gccggcccgg agtgcgaccg ctgcaagccc     960

ttccactacg accggccctg gcagcgcgcc acagcccgcg aagccaacga gtgcgtggcc    1020

tgtaactgca acctgcatgc ccggcgctgc cgcttcaaca tggagctcta caagctttcg    1080

gggcgcaaga gcggaggtgt ctgcctcaac tgtcgccaca acaccgccgg ccgccactgc    1140

cattactgca aggagggcta ctaccgcgac atgggcaagc ccatcaccca ccggaaggcc    1200

tgcaaagcct gtgattgcca ccctgtgggt gctgctggca aaacctgcaa ccaaaccacc    1260

ggccagtgtc cctgcaagga cggcgtgacg ggtatcacct gcaaccgctg cgccaaaggc    1320

taccagcaga gccgctctcc catcgccccc tgcataaaga tccctgtagc gccgccgacg    1380

actgcagcca gcagcgtgga ggagcctgaa gactgcgatt cctactgcaa ggcctccaag    1440

gggaagctga agattaacat gaaaaagtac tgcaagaagg actatgccgt ccagatccac    1500

atcctgaagg cggacaaggc gggggactgg tggaagttca cggtgaacat catctccgtg    1560

tataagcagg gcacgagccg catccgccgc ggtgaccaga gcctgtggat ccgctcgcgg    1620
```

```
gacatcgcct gcaagtgtcc caaaatcaag cccctcaaga agtacctgct gctgggcaac   1680

gcggaggact ctccggacca gagcggcatc gtggccgata aaagcagcct ggtgatccag   1740

tggcgggaca cgtgggcgcg gcggctgcgc aagttccagc agcgtgagaa gaagggcaag   1800

tgcaagaagg cctagcg                                                  1817


<210> SEQ ID NO 3
<211> LENGTH: 43
<212> TYPE: PRT
<213> ORGANISM: Homo sapiens

<400> SEQUENCE: 3

Val Ala Cys Asn Cys Asn Leu His Ala Arg Arg Cys Arg Phe Asn Met
1               5                   10                  15

Glu Leu Tyr Lys Leu Ser Gly Arg Lys Ser Gly Gly Val Cys Leu Asn
            20                  25                  30

Cys Arg His Asn Thr Ala Gly Arg His Cys His
        35                  40


<210> SEQ ID NO 4
<211> LENGTH: 129
<212> TYPE: DNA
<213> ORGANISM: Homo sapiens

<400> SEQUENCE: 4

gtggcctgta actgcaacct gcatgcccgg cgctgccgct tcaacatgga gctctacaag     60

ctttcggggc gcaagagcgg aggtgtctgc ctcaactgtc gccacaacac cgccggccgc    120

cactgccat                                                            129


<210> SEQ ID NO 5
<211> LENGTH: 8
<212> TYPE: PRT
<213> ORGANISM: Mus musculus

<400> SEQUENCE: 5

Gly Tyr Thr Phe Thr Ser Tyr Asn
1               5


<210> SEQ ID NO 6
<211> LENGTH: 8
<212> TYPE: PRT
<213> ORGANISM: Mus musculus

<400> SEQUENCE: 6

Ile Tyr Pro Gly Asn Gly Asp Thr
1               5


<210> SEQ ID NO 7
<211> LENGTH: 9
<212> TYPE: PRT
<213> ORGANISM: Mus musculus

<400> SEQUENCE: 7

Ala Arg Gly Gly Thr Gly Phe Ala Tyr
1               5


<210> SEQ ID NO 8
<211> LENGTH: 6
<212> TYPE: PRT
<213> ORGANISM: Mus musculus
```

<400> SEQUENCE: 8

```
Gln Ser Val Ser Asn Asp
1               5
```

<210> SEQ ID NO 9
<211> LENGTH: 9
<212> TYPE: PRT
<213> ORGANISM: Mus musculus

<400> SEQUENCE: 9

```
Gln Gln Asp Tyr Ser Ser Pro Trp Thr
1               5
```

<210> SEQ ID NO 10
<211> LENGTH: 116
<212> TYPE: PRT
<213> ORGANISM: Mus musculus
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 10

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Thr Gly Phe Ala Tyr Trp Gly Gln Gly Thr Leu Val
            100                 105                 110

Thr Val Ser Ala
        115
```

<210> SEQ ID NO 11
<211> LENGTH: 107
<212> TYPE: PRT
<213> ORGANISM: Mus musculus
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

```
<400> SEQUENCE: 11

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105


<210> SEQ ID NO 12
<211> LENGTH: 440
<212> TYPE: PRT
<213> ORGANISM: Mus musculus
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 12

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Thr Gly Phe Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Glu Ser Asp
                165                 170                 175

Leu Tyr Thr Leu Ser Ser Ser Val Thr Val Pro Ser Ser Pro Arg Pro
            180                 185                 190
```

```
Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
    370                 375                 380

Lys Asn Thr Gln Pro Ile Met Asn Thr Asn Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440


<210> SEQ ID NO 13
<211> LENGTH: 214
<212> TYPE: PRT
<213> ORGANISM: Mus musculus
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 13

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60
```

```
Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 14
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 14

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Asp Tyr Ser Ser Pro Trp
                85                  90                  95

Thr Phe Gly Gln Gly
            100


<210> SEQ ID NO 15
<211> LENGTH: 101
<212> TYPE: PRT
<213> ORGANISM: Artificial Sequence
```

```
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Phe Gln Gln Arg Pro Gly Gln Ser Pro Arg Arg Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asp Tyr Ser Ser Pro Trp
                85                  90                  95

Thr Phe Gly Gln Gly
            100


<210> SEQ ID NO 16
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80
```

```
Glu Asp Ala Ala Tyr Tyr Phe Cys Gln Gln Asp Tyr Ser Ser Pro Trp
                85                  90                  95

Thr Phe Gly Gln Gly
            100


<210> SEQ ID NO 17
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asp Tyr Ser Ser Pro Trp
                85                  90                  95

Thr Phe Gly Gln Gly
            100


<210> SEQ ID NO 18
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Lys Ala Ser Gln Ser Val Ser Asn Asp
            20                  25                  30
```

```
Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Asp Tyr Ser Ser Pro Trp
                85                  90                  95

Thr Phe Gly Gln Gly
            100


<210> SEQ ID NO 19
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 19

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Ser Ser Pro Trp
                85                  90                  95

Thr Phe Gly Gln Gly
            100


<210> SEQ ID NO 20
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT
```

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln Gly
            100                 105
```

<210> SEQ ID NO 21
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 21

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Tyr Thr Phe Thr Ser Tyr
            20                  25                  30

Asn Met His Trp Ile Arg Gln Pro Pro Gly Lys Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln Gly
            100                 105
```

<210> SEQ ID NO 22
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 22

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Thr Gly Phe Ala Tyr Trp Gly Gln Gly
            100                 105
```

<210> SEQ ID NO 23
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 23

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Gly Gly Thr Gly Phe Ala Tyr Trp Gly Gln Gly
            100                 105
```

```
<210> SEQ ID NO 24
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr Gly Phe Ala Tyr Trp Gly Gln Gly
            100                 105


<210> SEQ ID NO 25
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln Gly
            100                 105


<210> SEQ ID NO 26
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln Gly
            100                 105


<210> SEQ ID NO 27
<211> LENGTH: 108
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45
```

```
Gly Ala Ile Tyr Pro Gly Asn Gly Asp Thr Ser Tyr Ala Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln
            100                 105


<210> SEQ ID NO 28
<211> LENGTH: 5
<212> TYPE: PRT
<213> ORGANISM: Mus musculus

<400> SEQUENCE: 28

Ser Tyr Asn Met His
1               5


<210> SEQ ID NO 29
<211> LENGTH: 17
<212> TYPE: PRT
<213> ORGANISM: Mus musculus

<400> SEQUENCE: 29

Ala Ile Tyr Pro Gly Asn Gly Asp Thr Ser Tyr Asn Gln Lys Phe Lys
1               5                   10                  15

Gly


<210> SEQ ID NO 30
<211> LENGTH: 7
<212> TYPE: PRT
<213> ORGANISM: Mus musculus

<400> SEQUENCE: 30

Gly Gly Thr Gly Phe Ala Tyr
1               5


<210> SEQ ID NO 31
<211> LENGTH: 11
<212> TYPE: PRT
<213> ORGANISM: Mus musculus

<400> SEQUENCE: 31

Lys Ala Ser Gln Ser Val Ser Asn Asp Val Ala
1               5                   10


<210> SEQ ID NO 32
<211> LENGTH: 7
<212> TYPE: PRT
<213> ORGANISM: Mus musculus

<400> SEQUENCE: 32

Tyr Ala Ser Asn Arg Tyr Thr
1               5


<210> SEQ ID NO 33
<211> LENGTH: 25
<212> TYPE: DNA
<213> ORGANISM: Artificial Sequence
<220> FEATURE:
<223> OTHER INFORMATION: forward primer for PCR of human netrin-1 gene
```

-continued

```
<400> SEQUENCE: 33

aaaagtactg caagaaggac tatgc                                          25


<210> SEQ ID NO 34
<211> LENGTH: 21
<212> TYPE: DNA
<213> ORGANISM: Artificial Sequence
<220> FEATURE:
<223> OTHER INFORMATION: reverse primer for PCR of human netrin-1 gene

<400> SEQUENCE: 34

ccctgcttat acacggagat g                                              21


<210> SEQ ID NO 35
<211> LENGTH: 22
<212> TYPE: PRT
<213> ORGANISM: Homo sapiens

<400> SEQUENCE: 35

Ala Arg Arg Cys Arg Phe Asn Met Glu Leu Tyr Lys Leu Ser Gly Arg
1               5                   10                  15

Lys Ser Gly Gly Val Cys
            20


<210> SEQ ID NO 36
<211> LENGTH: 66
<212> TYPE: DNA
<213> ORGANISM: Homo sapiens

<400> SEQUENCE: 36

gcccggcgct gccgcttcaa catggagctc tacaagcttt cggggcgcaa gagcggaggt     60

gtctgc                                                               66
```

ANTI-NETRIN-1 ANTIBODY

The present invention relates to a netrin-1 binding polypeptide or antibody which is useful in inducing cell death or apoptosis of tumor cells bearing a netrin-1 receptor such as an UNC5 receptor in the presence of netrin-1, in particular the tumor express netrin-1, and its use for the treatment of cancer.

Netrin-1 is a member of the netrin family and is an axon navigation cue, both, in an attractive and repulsive context and plays a major role in the development of the nervous system. The main receptors for netrin-1 are DCC (Deleted in Colorectal Cancer) and UNC5 (UNC5A, UNC5B, UNC5C, UNC5D in human, UNC5H1, UNC5H2, UNC5H3, UNC5H4 in mice), which all belong to the dependence receptor family (Keino-Masu, 1996, Cell 87: 175-185; Ackermann, 1997, Nature 386: 838-842; Hong, 1999, Cell 97: 927-941; Mehlen, 1998, Nature 395: 801-804). Dependence receptors share the ability to induce apoptosis in the absence of their respective ligands, whereby this ability is blocked upon binding of the respective ligand (Mehlen, 2004, Cell Mol Life Sci 61: 1854-1866; Bredesen, 2005, Cell Death Differ 12: 1031-1043).

In various human cancers, reduction or loss of expression of DCC and, thus, reduction or loss of DCC-induced apoptosis has been observed (Kinzler, 1996, Proc Natl Acad Sci 100: 4173-4178). Furthermore, it has been observed that also UNC5 genes are downregulated in most colorectal tumors, indicating that the loss of dependence receptor UNC5 represents a selective advantage for tumor cells (Bernet, 2007, Gastroenterology 133: 180-1848; Shin, 2007, Gastroenterology 133: 1849-1857). However, not only down-regulation of the dependence receptor DCC and UNC5 enhances survival of various tumor cells, autocrine expression of their ligand netrin-1 has been observed. Particularly, it has been shown that the majority of breast tumors, i.e. metastatic breast cancers, exhibit increased expression of netrin-1 (Fitamant, 2008, Proc Natl Acad Sci 105: 4850-4855). Up to now, it has been demonstrated that the two Immunoglobulin (Ig) subdomains of the extracellular part of UNC5 are responsible for binding of netrin-1, but it is not clear whether both domains are necessary to full netrin-1 binding (Geisbrecht, 2003, J. Biol. Chem. 278: 32561-32568; Kruger, 2004, J. Neur. 24: 10826-10834).

As has been shown previously, neutralization of netrin-1 by the ectodomain of DCC or part of this ectodomain (acting as netrin-1 decoy protein) can induce apoptosis in tumor cells expressing dependence receptors DCC and/or UNC5 (EP-A1-1 989 546). This ectodomain or part of this ectodomain is capable to reduce metastasis of breast cancer cells into the lung (Fitamant et al. 2008). Furthermore, this ectodomain or part of this ectodomain has been also demonstrated to increase the cell death percentage of non-small cell lung cancer cells and neuroblastoma cells expressing high levels of netrin-1 (Delloye-Bourgeois, 2009, J Natl Cancer Inst 101: 237-247; Delloye-Bourgeois, 2009, JEM 206: 833-847). WO2012025618 discloses DCC-fusion proteins having improved DCC decoy.

EP 1 989 546 (WO2007099133) discloses monoclonal or polyclonal antibodies directed specifically against netrin-1 or netrin-1 receptors, particularly directed to the extracellular domain of the netrin-1 receptors or to the netrin-1 fragment able to interact with the extracellular domain of said netrin-1 receptors, as a medicament.

The Applicant has now determined a linear or substantially linear epitope on netrin-1 that likely corresponds to the specific binding region of netrin-1 to receptors, in particular of the UNC5 class, especially UNC5B and UNC5A, or alternatively corresponds to a region nearby the specific binding region of netrin-1 to receptor that when bound to an antibody prevents netrin-1/receptor interaction. This determination of a linear epitope allows the Applicant to produce antibodies binding to netrin-1 and interfering with netrin-1/receptors interaction, thereby inducing apoptosis or cell death of tumour cells expressing or overexpressing netrin-1 and at least one netrin-1 receptor, owing the fact that this interaction inhibits netrin-1 binding to a receptor and the multimerization of the receptor. The Applicant also produced a murine monoclonal antibody directed against this epitope and various humanized forms thereof.

The full-length amino acid sequence of netrin-1 is given as SEQ ID NO: 1 and a cDNA coding therefore is given at SEQ ID NO: 2. A linear epitope has been characterized in the second EGF-like domain of netrin-1 and is depicted on SEQ ID NO: 3 and more particularly on SEQ ID NO:35. A cDNA encoding this epitope is depicted on SEQ ID NO: 4, respectively 36.

A first object of the invention is thus a polypeptide representing a linear epitope of netrin-1 or a fragment or variant of said linear epitope. More specifically, the invention relates to:

- an isolated or purified polypeptide of sequence SEQ ID NO: 3,
- a variant polypeptide having at least 85, 90, 95, 96, 97, 98 or 99% of identity to SEQ ID NO: 3,
- a variant polypeptide of at most 200, 150, 100, 90, 80, 70, 60, 50 amino acids and comprising SEQ ID NO: 3 or variant sequence as described above, such as a variant polypeptide consisting of the 22 consecutive amino acids of SEQ ID NO: 3 from position 9 (A) to position 30 (C), including these amino acids, which variant is presented as SEQ ID NO: 35,
- a variant polypeptide comprising at least 20, 25 or 30 consecutive amino acids of SEQ ID NO: 3 such as a variant polypeptide of sequence SEQ ID NO: 35, or variant sequence as described above,
- a polypeptide of sequence SEQ ID NO: 35, or variant sequence as described above,
- an isolated or purified polypeptide encoded by the cDNA of sequence SEQ ID NO: 4 or 36.

Another object of the invention is a cDNA coding for said polypeptide representing a linear epitope of netrin-1 or a fragment or variant of said linear epitope. More specifically, the invention relates to:

- a cDNA of sequence SEQ ID NO: 4,
- a variant cDNA encoding the polypeptide of sequence SEQ ID NO: 3 or a variant thereof, by virtue of the degeneracy of the genetic code,
- a variant cDNA encoding a variant polypeptide as defined earlier, especially a cDNA encoding the variant polypeptide SEQ ID NO: 35, such as cDNA of SEQ ID NO: 36,
- a variant cDNA having at least 85, 90, 95, 96, 97, 98 or 99% of identity to SEQ ID NO: 4 or 36.

In accordance with the invention, a variant polypeptide is able to generate an antibody which still keeps the ability to specifically bind to the linear epitope on netrin-1 and inhibit the interaction of netrin-1 to its receptor, in particular UNC5 or DCC, especially UNC5B and UNC5A, and induce apoptosis or cell death of the tumour cell expressing or overexpressing netrin-1 and a netrin-1 receptor. A variant cDNA codes for the polypeptide of SEQ ID NO: 3 or of SEQ ID NO: 35 or for a variant polypeptide.

Another object of the invention is the use of the polypeptide of SEQ ID NO: 3 or 35 or a variant thereof, to produce a monoclonal antibody, and the monoclonal antibodies so produced are also an object of the invention. The person skilled in the art is aware of the methods allowing producing monoclonal antibodies, using the plasmocyte and hybridoma technique. The invention encompasses the use of these methods to produce antibodies specifically directed against the polypeptide of SEQ ID NO: 3 or 35 or a variant thereof. It is also within the scope of the invention to produce polypeptides or monoclonal antibodies through genetic engineering based on nucleic acid sequences coding for the specific polypeptide or antibody, owing the determination and disclosure of the CDRs of the VH and VL. It is also within the scope of the invention to provide for antibody fragments and/or humanized antibodies or antibody fragments with a variable region specific to the linear epitope of the invention, a fragment or a variant thereof. The term "binding polypeptide" will be used herein to encompass antibodies and antibody variants, fragments and combination that keep the binding function of the antibody.

The present invention thus also relates to a netrin-1 binding polypeptide which specifically binds to a polypeptide having the amino acid sequence SEQ ID NO: 3 or 35 or a variant thereof. The binding polypeptide has the property of binding to netrin-1 and induce cell death or apoptosis of a tumor cell via an UNC5 or DCC receptor. The fact is that free or active netrin-1 does no longer exist or at an insufficient level, so that the apoptosis signaling of the netrin-1 receptor is activated.

The present invention also relates to a netrin-1 binding polypeptide which comprises one or more complementarity-determining region(s) (CDR(s)) having an amino acid sequence SEQ ID NO: 7, SEQ ID NO: 30 or SEQ ID NO: 9, wherein the binding polypeptide has the property of binding to netrin-1 and inducing cell death or apoptosis of a tumor cell via an UNC5 or DCC receptor.

The polypeptide may be an antibody or an epitope-binding fragment thereof.

Using the IMGT definition, the present invention thus relates to a netrin-1 binding polypeptide which comprises one or more complementarity-determining region (CDR) having an amino acid sequence SEQ ID NO: 7 (CDR3-H), SEQ ID NO: 9 (CDR3-L), and preferably both.

More specifically, the polypeptide may be further defined by the additional presence of CDR1, CDR2 or the CDR1 and CDR2 of the VH and/or VL. Therefore, the polypeptide may comprise one or more CDR(s) having the amino acid sequences SEQ ID NO: 7 and SEQ ID NO: 5; SEQ ID NO: 7 and SEQ ID NO: 6; SEQ ID NO: 9 and the sequence YAS; and/or SEQ ID NO: 9 and SEQ ID NO: 8.

An object of the invention is a polypeptide comprising a CDR1-H of sequence SEQ ID NO: 5, a CDR2-H of sequence SEQ ID NO: 6, a CDR3-H of sequence SEQ ID NO: 7.

An object of the invention is a polypeptide comprising a CDR1-L of sequence SEQ ID NO: 8, a CDR2-L of sequence YAS and a CDR3-L of sequence SEQ ID NO: 9.

The polypeptide of the invention preferably comprises a CDR1-H of sequence SEQ ID NO: 5, a CDR2-H of sequence SEQ ID NO: 6, a CDR3-H of sequence SEQ ID NO: 7, a CDR1-L of sequence SEQ ID NO: 8, a CDR2-L of sequence YAS and a CDR3-L of sequence SEQ ID NO: 9.

Using the Kabat definition, the present invention thus relates to a netrin-1 binding polypeptide which comprises one or more complementarity-determining region (CDR) having an amino acid sequence SEQ ID NO: 30 (CDR3-H), SEQ ID NO: 9 (CDR3-L), and preferably both.

More specifically, the polypeptide may be further defined by the additional presence of CDR1, CDR2 or the CDR1 and CDR2 of the VH and/or VL. Therefore, the polypeptide may comprise one or more CDR(s) having the amino acid sequences SEQ ID NO: 30 and SEQ ID NO: 28; SEQ ID NO: 30 and SEQ ID NO: 29; SEQ ID NO: 9 and the SEQ ID NO: 32; and/or SEQ ID NO: 9 and SEQ ID NO: 31.

An object of the invention is a polypeptide comprising a CDR1-H of sequence SEQ ID NO: 28, a CDR2-H of sequence SEQ ID NO: 29, a CDR3-H of sequence SEQ ID NO: 30.

An object of the invention is a polypeptide comprising a CDR1-L of sequence SEQ ID NO: 31, a CDR2-L of sequence SEQ ID NO: 32 and a CDR3-L of sequence SEQ ID NO: 9.

The polypeptide of the invention preferably comprises a CDR1-H of sequence SEQ ID NO: 28, a CDR2-H of sequence SEQ ID NO: 29, a CDR3-H of sequence SEQ ID NO: 30, a CDR1-L of sequence SEQ ID NO: 31, a CDR2-L of sequence SEQ ID NO:32 and a CDR3-L of sequence SEQ ID NO: 9.

These polypeptides are netrin-1 binding polypeptides, wherein the binding polypeptide has the property of binding to netrin-1 and induce cell death or apoptosis of a tumor cell via an UNC5 or DCC receptor. These polypeptides are preferably antibodies, especially monoclonal antibodies. Various forms of binding polypeptides or antibodies (including fragments and combination thereof) will be described later herein.

In a first series of embodiments, the polypeptide or antibody of the invention comprises an amino acid sequence SEQ ID NO: 10, 11, 12 or 13. Typically, it comprises both sequences SEQ ID NO: 10 and 11, or SEQ ID NO: 12 and 13.

In a second series of embodiments, the polypeptide or antibody is humanized and comprises an amino acid sequence selected from the group of SEQ ID NO: 14 to 19 and/or from the group of SEQ ID NO: 20 to 27. Typically, the polypeptide or antibody is humanized and comprises an amino acid sequence selected from the group of SEQ ID NO: 14 to 19 and an amino acid sequence selected from the group of SEQ ID NO: 20 to 27.

Specific embodiments are the following humanized antibodies. The first listed in this table correspond to the grafting of the murine CDRs into a human IgG1. The others called HUM are monoclonal antibodies having variable human framework regions. The table gives also a reference for the CH and CL of a human IgG1. The other allotypes may be used as well.

| | VH SEQ ID NO: | Constant heavy chain | VL SEQ ID NO: | Constant light chain |
|---|---|---|---|---|
| CDR graft (murine CDRs grafted into human IgG1) | 19 | Human IgG1 (GenBank: AEL33691.1 modified R97K) | 27 | Human IgG1 (GenBank: CAC20459.1) |
| HUM01 | 20 | Human IgG1 | 14 | Human IgG1 |
| HUM02 | 21 | Human IgG1 | 15 | Human IgG1 |
| HUM03 | 22 | Human IgG1 | 16 | Human IgG1 |
| HUM04 | 23 | Human IgG1 | 17 | Human IgG1 |
| HUM05 | 24 | Human IgG1 | 17 | Human IgG1 |
| HUM06 | 25 | Human IgG1 | 16 | Human IgG1 |
| HUM07 | 26 | Human IgG1 | 17 | Human IgG1 |
| HUM08 | 22 | Human IgG1 | 17 | Human IgG1 |

-continued

| | VH SEQ ID NO: | Constant heavy chain | VL SEQ ID NO: | Constant light chain |
|---|---|---|---|---|
| HUM09 | 25 | Human IgG1 | 18 | Human IgG1 |
| HUM10 | 21 | Human IgG1 | 16 | Human IgG1 |

Another object of the invention is a pharmaceutical composition comprising at least one netrin-1 binding polypeptide or antibody according to the invention and a pharmaceutically acceptable vehicle or excipient. In an embodiment, the polypeptide or antibody is humanized.

Still another object of the invention is a method of treatment of cancer wherein a subject in need thereof is administered with a therapeutically effective amount of a pharmaceutical composition comprising at least one netrin-1 binding polypeptide or antibody according to the invention and a pharmaceutically acceptable vehicle or excipient. In an embodiment, the polypeptide or antibody is humanized.

Thus the composition and method may comprise any one of the features or combination of features as disclosed with respect to the polypeptide or antibody as disclosed herein.

According to a feature, the cancer is one wherein tumoral cells express or over-express a netrin-1 receptor, in particular of the UNC5 class, especially UNC5B and/or UNC5A, and/or DCC. Typically the tumoral cells escape netrin-1 receptor related apoptosis owing binding of netrin-1 to said receptor, in particular of the UNC5 class, especially UNC5B and/or UNC5A, and/or DCC, in the presence of netrin-1. According to a feature, the cancer is one wherein tumoral cells or stromal cells express or over-express netrin-1.

Some embodiments of cancers include metastatic breast cancer, non-small cell lung cancer, aggressive neuroblastoma, pancreatic adenocarcinoma, primary melanoma, melanoma metastasis, ovarian cancers, glioblastoma, acute myeloid leukaemia, chronic lymphocytic leukaemia, aggressive B-cell lymphoma, sarcoma, renal adenocarcinoma, head and neck cancers, testicular cancers (e.g. embryonal carcinoma, teratoma, yolk sac tumors), kidney cancers, stomach cancers, uterus cancers Methods of determining whether a given cell expresses netrin-1 dependence receptors DCC and/or UNC5 on the surface or shows significant up-regulation of netrin-1 gene expression are well known in the art and comprise, but are not limited to, IHC (Immunohistochemistry) of FACS (Fluorescence activated cell sorting), quantitative PCR (e.g. with hexamer primed cDNA) or alternatively Western Blot paired with chromogenic dye-based protein detection techniques (such as silver or coomassie blue staining) or fluorescence- and luminescence-based detection methods for proteins in solutions and on gels, blots and microarrays, such as immunostaining, as well as immunoprecipitation, ELISA, microarrays, and mass spectrometry. In the context of the present invention, examples for cancers to be treated are listed herein including refractory versions of any of the mentioned cancers. Netrin-1 overexpression may thus be measured through RT-PCR using suitable primers as those disclosed and provided herein, with respect to normal tissue or to a similar cancer which does not overexpress netrin-1.

In an embodiment of the invention, the compositions and methods are for the treatment of cancers expressing or over-expressing netrin-1, wherein this expression or over-expression is linked to the cancer itself, or is induced by a chemotherapeutic drug treatment alone, or both.

An object of the invention is a method of combined anti-cancer treatment comprising the administration to a patient in need thereof of a chemotherapeutic drug and of a polypeptide or antibody as disclosed herein. The chemotherapeutic drug and the polypeptide or antibody is in effective amount.

Another object of the invention is a composition comprising a polypeptide or antibody as disclosed herein for use as an anti-cancer medicament to be used in combination with a chemotherapeutic drug in a patient. The invention also relates to a composition comprising a polypeptide or antibody as disclosed herein for use as an anti-cancer medicament in a patient who is treated with a chemotherapeutic drug.

Another object of the invention is a composition comprising a chemotherapeutic drug for use as an anti-cancer medicament to be used in a patient in combination with a polypeptide or antibody as disclosed herein. The invention also relates to a composition comprising a chemotherapeutic drug for use as an anti-cancer medicament in a patient who is treated with a polypeptide or antibody as disclosed herein.

Another object of the invention is a composition or kit of parts comprising a chemotherapeutic drug and a polypeptide or antibody as disclosed herein, for a simultaneous, separate or sequential administration to a patient.

Another object of the invention is a composition or kit of parts comprising a chemotherapeutic drug and a polypeptide or antibody as disclosed herein, for a simultaneous, separate or sequential administration to a patient, for use as an anti-cancer medicament or anti-cancer treatment.

Another object of the invention is a composition comprising a chemotherapeutic drug and a polypeptide or antibody as disclosed herein, in a pharmaceutically acceptable carrier or vehicle.

Another object of the invention is a composition comprising a chemotherapeutic drug and a polypeptide or antibody as disclosed herein, in a pharmaceutically acceptable carrier or vehicle, for use as an anti-cancer medicament.

Still another object is the use of a polypeptide or antibody as disclosed herein for the preparation of an anti-cancer medicament intended for a combined treatment of a patient with a chemotherapeutic drug.

Still another object is the use of a chemotherapeutic drug for the preparation of an anti-cancer medicament intended for a combined treatment of a patient with a polypeptide or antibody as disclosed herein.

Still another object is the use of a polypeptide or antibody as disclosed herein and a chemotherapeutic drug for the preparation of a combined anti-cancer medicament.

Still another object is the use of a polypeptide or antibody as disclosed herein and a chemotherapeutic drug for the preparation of a combined anti-cancer medicament composition or kit of parts, for a simultaneous, separate or sequential administration to a patient.

In accordance with a feature of the invention and as further explained below, the chemotherapeutic drug is a drug which induces an over-expression of netrin-1 in cancer cells and the polypeptide or antibody as disclosed herein promotes netrin-1 receptors-induced apoptosis or cell death despite this overexpression.

The chemotherapeutic drug is in particular a drug which induces an over-expression of netrin-1 in cancer cells. The determination that a drug induces a netrin-1 over-expression may be easily performed on any cancerous cell, such as cell line or cells from a biopsy. In an embodiment, the assay is performed on cells from the cancer to be treated, for example from a biopsy. In another embodiment, the assay is performed on a cell, such as a cell line, which is representative for the cancer to be treated. In another embodiment, the assay is made on a A549 or H460 cell line. The assay may comprise comparing the netrin-1 gene expression between the cells treated with the chemotherapeutic drug and the cells not treated. The expression may be measured by PCR, especially quantitative RT-PCR, for example using the primers disclosed and provided herein (SEQ ID NO: 33 and 34) as described in PCT/EP2013/068937, the whole content of which is incorporated by reference or the skilled person may refer. The classification of a drug in the family of those inducing this over-expression may simply be performed in accordance with the method described in the following Material and Method on a A549 or H460 cell line, as described in PCT/EP2013/068937.

The chemotherapeutic drug is especially a cytotoxic drug. In some preferred embodiments, the drug is doxorubicin, 5-fluorouracil (5FU), paclitaxel (e.g. TAXOL®), or cisplatin.

In an embodiment, the drug is a cytotoxic antibiotic. The cytotoxic antibiotic may be actinomycin, an anthracycline, bleomycin, plicamycin or mitomycin. The anthracycline may be doxorubicin, daunorubicin, valrubicin, idarubicine or epirubicine.

In an embodiment, the drug is an alkylating agent. The alkylating agent may be a platinum derivative, such as cisplatin, carboplatin, oxaliplatine or other alkylating agents such as cyclophosphamide, ifosfamide, melphalan, thiotepa. Other classes include-epipodophylotoxines, e.g. etoposide, topoisomerase inhibitors (camptotecines), e.g. irinotecan, topotecan, alkylating agents of the minor groove of DNA, e.g. Trabectedine (YONDELIS), methotrexate, pemetrexed, raltitrexed.

In an embodiment, the drug is a taxane or other tubulin targeting agents. The taxane may be paclitaxel or docetaxel, or eribuline (recently approved for breast cancer).

In an embodiment, the drug is an antineoplastic agent such as:

- breast hormonotherapy agents: e.g. tamoxifene, letrozole, anastrozole, exemestane, FASLODEX®;
- prostate hormonotherapy agents: e.g. LHRH agonists, bicalutamide, abiraterone;
- monoclonal antibodies: e.g. cetuximab, panitumumab, bevacizumab;
- kinase inhibitors: e.g. imatinib, nilotinib, dasatinib, erlotinib, gefitinib, afatinib, sunitinib, sorafenib, pazopanib, crizotinib, axitinib.

Definitions and further embodiments, variants and alternatives of the invention:

As used herein, a sequence "at least 85% identical to a reference sequence" is a sequence having, on its entire length, 85%, or more, in particular 90%, 91%, 92%, 93%, 94%, 95%, 96%, 97%, 98%, 99%, 99.5%, 99.6%, 99.7%, 99.8%, 99.9% or 100% sequence identity with the entire length of the reference sequence.

A percentage of "sequence identity" may be determined by comparing the two sequences, optimally aligned over a comparison window, wherein the portion of the polypeptide sequence in the comparison window may comprise additions or deletions (i.e. gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison is conducted by global pairwise alignment, e.g. using the algorithm of Needleman and Wunsch (1970) *J. Mol. Biol.* 48: 443. The percentage of sequence identity can be readily determined for instance using the program Needle, with the BLOSUM62 matrix, and the following parameters gap-open=10, gap-extend=0.5.

In the context of the invention, a "conservative amino acid substitution" is one in which an amino acid residue is substituted by another amino acid residue having a side chain group with similar chemical properties (e.g., charge or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine-tryptophane, lysine-arginine, alanine-valine, glutamate-aspartate, and asparagine-glutamine.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

An "antibody" may be a natural or conventional antibody in which two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site.

"Complementarity Determining Regions" or "CDRs" refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody.

In the context of the invention, CDR/FR definition in an immunoglobulin light or heavy chain is to be determined based on IMGT definition (Lefranc et al. (2003) *Dev Comp Immunol.* 27(1):55-77).

As used herein, the term "antibody" denotes conventional antibodies and fragments thereof, as well as single domain antibodies and fragments thereof, in particular variable heavy chain of single domain antibodies, and chimeric, humanised, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard (Harmsen and De Haard (2007) Appl. Microbiol. Biotechnol. 77:13-22).

The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

"Fragments" of (conventional) antibodies comprise a portion of an intact antibody, in particular the antigen binding region or variable region of the intact antibody. Examples of antibody fragments include Fv, Fab, $F(ab')_2$, Fab', dsFv, $(dsFv)_2$, scFv, $sc(Fv)_2$, diabodies, bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

The term "$F(ab')_2$" refers to an antibody fragment having a molecular weight of about 100,000 Da and antigen binding activity, which is slightly larger than the Fab bound via a disulfide bond of the hinge region, among fragments obtained by treating IgG with a protease, pepsin.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent $sc(Fv)_2$.

"dsFv" is a VH::VL heterodimer stabilised by a disulphide bond.

"$(dsFv)_2$" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

In a particular embodiment, the epitope-binding fragment is selected from the group consisting of Fv, Fab, $F(ab')_2$, Fab', dsFv, $(dsFv)_2$, scFv, $sc(Fv)_2$, diabodies and VHH.

A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass.

The term "humanised antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin. As used herein, the term "humanized antibody" refers to a chimeric antibody which contain minimal sequence derived from non-human immunoglobulin, e.g. the CDRs.

The term "polypeptide" or "netrin-1 binding polypeptide" is used to encompass all these kinds of antibodies, fragments or combination thereof.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Antibodies can be humanized using a variety of other techniques including CDR-grafting (EP0239400; WO91/09967; U.S. Pat. Nos. 5,530,101 and 5,585,089), veneering or resurfacing (EP0592106; EP0519596; Padlan (1991) *Molecular Immunology* 28(415):489-498; Studnicka et al. (1994) *Protein Engineering* 7(6):805-814; Roguska et al. (1994) *Proc. Natl. Acad. Sci U.S.A.* 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and International patent application WO98/46645, WO98/50433, WO98/24893, WO98/16654, WO96/34096, WO96/33735, and WO91/10741.

In the context of the invention, the term "treating" or "treatment", as used herein, means reversing, alleviating, inhibiting the progress of, or preventing the disorder or condition to which such term applies, or one or more symptoms of such disorder or condition.

By the term "treating cancer" as used herein is meant the inhibition of the growth of malignant cells of a tumour and/or the progression of metastases from said tumor. Such treatment can also lead to the regression of tumor growth, i.e., the decrease in size of a measurable tumor. In a particular embodiment, such treatment leads to a partial regression of the tumor or metastasis. In another particular embodiment, such treatment leads to the complete regression of the tumor or metastasis.

According to the invention, the term "patient" or "patient in need thereof" is intended for a human or non-human mammal affected or likely to be affected with a malignant tumor.

In a particular embodiment, the patient to be treated may have been previously treated with other anti-cancer treatments. In particular, the patient to be treated may have been previously treated with an oxaliplatin-, cisplatin-, a carboplatin-, and/or a paclitaxel-docetaxel-based regimen.

By a "therapeutically effective amount" of the polypeptide or antibody of the invention is meant a sufficient amount thereof to treat said cancer disease, at a reasonable benefit/risk ratio applicable to any medical treatment. It will be understood, however, that the total daily usage of the polypeptide or antibody of the present invention will be decided by the attending physician within the scope of sound medical judgment. The specific therapeutically effective dose level for any particular patient will depend upon a variety of factors including the disorder being treated and the severity of the disorder; activity of the specific polypeptide or antibody employed; the specific composition employed, the age, body weight, general health, sex and diet of the patient; the time of administration, route of administration, and rate of excretion of the specific polypeptide or antibody employed; the duration of the treatment; drugs used in combination or coincidental with the specific polypeptide or antibody employed; and like factors well known in the medical arts. In a particular embodiment, said therapeutically effective amount of the polypeptide or antibody administered to the patient is a dose ranging from 5 $mg/m^2$ to 500 $mg/m^2$, more particularly ranging from 150 $mg/m^2$ to 450 $mg/m^2$ of body surface area.

In a further embodiment, the polypeptide or antibody of the invention is administered repeatedly according to a protocol that depends on the patient to be treated (age, weight, treatment history, etc.), which can be determined by a skilled physician.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions including the polypeptide or antibody of the invention and the route of administration naturally depend upon the condition to be treated, the severity of the illness, the age, weight, and gender of the patient, etc.

The polypeptide or antibody of the invention can be formulated for a topical, oral, parenteral, intranasal, intravenous, intramuscular, subcutaneous or intraocular administration and the like. In a particular embodiment, the polypeptide or antibody of the invention is administered intravenously In particular, the pharmaceutical compositions including the polypeptide or antibody of the invention may contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

To prepare pharmaceutical compositions, an effective amount of the polypeptide or antibody of the invention may be dissolved or dispersed in a pharmaceutically acceptable carrier or aqueous medium.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (for example, glycerol, propylene glycol, and liquid polyethylene glycol, and the like) and suitable mixtures thereof. The proper fluidity can be maintained, for example, by the use of a coating, such as lecithin, by the maintenance of the required particle size in the case of dispersion and by the use of surfactants, stabilizing agents, cryoprotectants or antioxidants. The prevention of the action of microorganisms can be brought about by antibacterial and antifungal agents. In many cases, it will be preferable to include isotonic agents, for example, sugars or sodium chloride.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

TABLE 1

Description of the sequences:

| SEQ ID NO: | Description | Sequence |
|---|---|---|
| 1 | Netrin-1 amino acid (aa) sequence (seq.) with signal peptide in bold and linear epitope mapping in bold and underlined | ***MMRAVWEALAALAAVACLVGAVRG***GPGLSMFAGQAAQ<br>PDPCSDENGHPRRCIPDFVNAAFGKDVRVSSTCGRPPA<br>RYCVVSERGEERLRSCHLCNASDPKKAHPPAFLTDLNNP<br>HNLTCWQSENYLQFPHNVTLTLSLGKKFEVTYVSLQFCS<br>PRPESMAIYKSMDYGRTWVPFQFYSTQCRKMYNRPHRA<br>PITKQNEQEAVCTDSHTDMRPLSGGLIAFSTLDGRPSAHD<br>FDNSPVLQDWVTATDIRVAFSRLHTFGDENEDDSELARD<br>SYFYAVSDLQVGGRCKCNGHAARCVRDRDDSLVCDCRH<br>NTAGPECDRCKPFHYDRPWQRATAREANEC**VACNCNL**<br>**HARRCRFNMELYKLSGRKSGGVCLNCRHNTAGRHCH**Y<br>CKEGYYRDMGKPITHRKACKACDCHPVGAAGKTCNQTT<br>GQCPCKDGVTGITCNRCAKGYQQSRSPIAPCIKIPVAPPT<br>TAASSVEEPEDCDSYCKASKGKLKINMKKYCKKDYAVQIH<br>ILKADKAGDWWKFTVNIISVYKQGTSRIRRGDQSLWIRSR<br>DIACKCPKIKPLKKYLLLGNAEDSPDQSGIVADKSSLVIQW<br>RDTWARRLRKFQQREKKGKCKKA |
| 2 | Netrin-1 nucleic acid seq. | ATGATGCGCGCAGTGTGGGAGGCGCTGGCGGCGCTG<br>GCGGCGGTGGCGTGCCTGGTGGGCGCGGTGCGCGG<br>CGGGCCCGGGCTCAGCATGTTCGCGGGCCAGGCGGC<br>GCAGCCCGATCCCTGCTCGGACGAGAACGGCCACCC<br>GCGCCGCTGCATCCCGGACTTTGTCAATGCGGCCTTC<br>GGCAAGGACGTGCGCGTGTCCAGCACCTGCGGCCGG<br>CCCCCGGCGCGCTACTGCGTGGTGAGCGAGCGCGGC<br>GAGGAGCGGCTGCGCTCGTGCCACCTCTGCAACGCGT<br>CCGACCCCAAGAAGGCGCACCCGCCCGCCTTCCTCAC<br>CGACCTCAACAACCCGCACAACCTGACGTGCTGGCAG<br>TCCGAGAACTACCTGCAGTTCCCGCACAACGTCACGCT<br>CACACTGTCCCTCGGCAAGAAGTTCGAAGTGACCTAC<br>GTGAGCCTGCAGTTCTGCTCGCCGCGGCCCGAGTCCA<br>TGGCCATCTACAAGTCCATGGACTACGGGCGCACGTG<br>GGTGCCCTTCCAGTTCTACTCCACGCAGTGCCGCAAG<br>ATGTACAACCGGCCGCACCGCGCGCCCATCACCAAGC<br>AGAACGAGCAGGAGGCCGTGTGCACCGACTCGCACAC<br>CGACATGCGCCCGCTCTCGGGCGGCCTCATCGCCTTC<br>AGCACGCTGGACGGGCGGCCCTCGGCGCACGACTTC<br>GACAACTCGCCCGTGCTGCAGGACTGGGTCACGGCCA<br>CAGACATCCGCGTGGCCTTCAGCCGCCTGCACACGTT<br>CGGCGACGAGAACGAGGACGACTCGGAGCTGGCGCG<br>CGACTCGTACTTCTACGCGGTGTCCGACCTGCAGGTG<br>GGCGGCCGGTGCAAGTGCAACGGCCACGCGGCCCGC<br>TGCGTGCGCGACCGCGACGACAGCCTGGTGTGCGACT<br>GCAGGCACAACACGGCCGGCCCGGAGTGCGACCGCT<br>GCAAGCCCTTCCACTACGACCGGCCCTGGCAGCGCGC<br>CACAGCCCGCGAAGCCAACGAGTGCGTGGCCTGTAAC<br>TGCAACCTGCATGCCCGGCGCTGCCGCTTCAACATGG<br>AGCTCTACAAGCTTTCGGGGCGCAAGAGCGGAGGTGT |

TABLE 1-continued

| SEQ ID NO: | Description | Sequence |
|---|---|---|
| | | CTGCCTCAACTGTCGCCACAACACCGCCGGCCGCCAC TGCCATTACTGCAAGGAGGGCTACTACCGCGACATGG GCAAGCCCATCACCCACCGGAAGGCCTGCAAAGCCTG TGATTGCCACCCTGTGGGTGCTGCTGGCAAAACCTGC AACCAAACCACCGGCCAGTGTCCCTGCAAGGACGGCG TGACGGGTATCACCTGCAACCGCTGCGCCAAAGGCTA CCAGCAGAGCCGCTCTCCCATCGCCCCCTGCATAAAG ATCCCTGTAGCGCCGCCGACGACTGCAGCCAGCAGCG TGGAGGAGCCTGAAGACTGCGATTCCTACTGCAAGGC CTCCAAGGGGAAGCTGAAGATTAACATGAAAAAGTACT GCAAGAAGGACTATGCCGTCCAGATCCACATCCTGAA GGCGGACAAGGCGGGGGACTGGTGGAAGTTCACGGT GAACATCATCTCCGTGTATAAGCAGGGCACGAGCCGC ATCCGCCGCGGTGACCAGAGCCTGTGGATCCGCTCGC GGGACATCGCCTGCAAGTGTCCCAAAATCAAGCCCCT CAAGAAGTACCTGCTGCTGGGCAACGCGGAGGACTCT CCGGACCAGAGCGGCATCGTGGCCGATAAAAGCAGCC TGGTGATCCAGTGGCGGGACACGTGGGCGCGGCGGC TGCGCAAGTTCCAGCAGCGTGAGAAGAAGGGCAAGTG CAAGAAGGCCTAGCG |
| 3 | Netrin-1 aa epitopic seq. | VACNCNLHARRCRFNMELYKLSGRKSGGVCLNCRHNTA GRHCH |
| 4 | Netrin-1 epitopic cDNA seq. | GTGGCCTGTAACTGCAACCTGCATGCCCGGCGCTGCC GCTTCAACATGGAGCTCTACAAGCTTTCGGGGCGCAA GAGCGGAGGTGTCTGCCTCAACTGTCGCCACAACACC GCCGGCCGCCACTGCCAT |
| 5 | aa seq. of CDR1-H (IMGT) | GYTFTSYN |
| 6 | aa seq. of CDR2-H (IMGT) | IYPGNGDT |
| 7 | aa seq. of CDR3-H (IMGT) | ARGGTGFAY |
| 8 | aa seq. of CDR1-L (IMGT) | QSVSND |
| — | aa seq. of CDR2-L (IMGT) | YAS |
| 9 | aa seq. of CDR3-L (IMGT et Kabat) | QQDYSSPWT |
| 10 | aa sequence of mouse 4C11 VH | QAYLQQSGAELVRPGASVKMSCKAS**GYTFTSYN**MHWVK QTPRQGLEWIGA**IYPGNGDT**SYNQKFKGKATLTVDKSSS TAYMQLSSLTSEDSAVYFC**ARGGTGFAY**WGQGTLVTVS A |
| 11 | aa sequence of mouse 4C11 VL | SIVMTQTPKFLLVSAGDRVTITCKAS**QSVSND**VAWYQQK PGQSPKLLIY**YAS**NRYTGVPDRFTGSGYGTDFTFTISTVQ AEDLAVYFC**QQDYSSPWT**FGGGTKLEIK |
| 12 | Full aa sequence of 4C11 (VH + mouse IgG1 CH) | QAYLQQSGAELVRPGASVKMSCKAS**GYTFTSYN**MHWVK QTPRQGLEWIGA**IYPGNGDT**SYNQKFKGKATLTVDKSSS TAYMQLSSLTSEDSAVYFC**ARGGTGFAY**WGQGTLVTVS AAKTTPPSVYPLAPGSAAQTNSMVTLGCLVKGYFPEPVT VTWNSGSLSSGVHTFPAVLESDLYTLSSSVTVPSSPRPS ETVTCNVAHPASSTKVDKKIVPRDCGCKPCICTVPEVSSV FIFPPKPKDVLTITLTPKVTCVVVDISKDDPEVQFSWFVDD VEVHTAQTQPREEQFNSTFRSVSELPIMHQDWLNGKEFK CRVNSAAFPAPIEKTISKTKGRPKAPQVYTIPPPKEQMAK DKVSLTCMITDFFPEDITVEWQWNGQPAENYKNTQPIMN TNGSYFVYSKLNVQKSNWEAGNTFTCSVLHEGLHNHHT EKSLSHSPGK |

TABLE 1-continued

Description of the sequences:

| SEQ ID NO: | Description | Sequence |
|---|---|---|
| 13 | Full aa sequence of 4C11 (VL + mouse Kappa CL) | SIVMTQTPKFLLVSAGDRVTITCKAS**QSVSND**VAWYQQKPGQSPKLLIY**YAS**NRYTGVPDRFTGSGYGTDFTFTISTVQAEDLAVYFC**QQDYSSPWT**FGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| 14 | VL aa sequence of humanized variant of 4C11 | EIVMTQSPATLSVSPGERATLSCKAS**QSVSND**VAWYQQKPGKAPKLLIY**YAS**NRYTGIPPRFSGSGYGTDFTLTINNIESEDAAYYFC**QQDYSSPWT**FGQG |
| 15 | VL aa sequence of humanized variant of 4C11 | DIQMTQSPSSLSASVGDRVTITCKAS**QSVSND**VAWFQQRPGQSPRRLIY**YAS**NRYTGVPSRFSGSGSGTDFTFTISSLEAEDAATYYC**QQDYSSPWT**FGQG |
| 16 | VL aa sequence of humanized variant of 4C11 | DIQMTQSPSSLSASVGDRVTITCKAS**QSVSND**VAWYQQKPGQAPRLLIY**YAS**NRYTGIPPRFSGSGYGTDFTLTINNIESEDAAYYFC**QQDYSSPWT**FGQG |
| 17 | VL aa sequence of humanized variant of 4C11 | DIQMTQSPSSLSASVGDRVTITCKAS**QSVSND**VAWYLQKPGQSPQLLIY**YAS**NRYTGVPSRFSGSGSGTDFTFTISSLEAEDAATYYC**QQDYSSPWT**FGQG |
| 18 | VL aa sequence of humanized variant of 4C11 | DIVMTQTPLSLPVTPGEPASISCKAS**QSVSND**VAWYQQKPGQAPRLLIY**YAS**NRYTGIPPRFSGSGYGTDFTLTINNIESEDAAYYFC**QQDYSSPWT**FGQG |
| 19 | VL aa sequence of humanized variant of 4C11 | EIVMTQSPATLSVSPGERATLSCRAS**QSVSND**VAWYQQKPGQAPRLLIY**YAS**NRYTGIPARFSGSGSGTEFTLTISSLQSEDFAVYYC**QQDYSSPWT**FGQG |
| 20 | VH aa sequence of humanized variant of 4C11 | QVQLVQSGAEVKKPGASVKVSCKAS**GYTFTSYN**MHWVRQATGQGLEWMGA**IYPGNGDT**SYNQKFKGRVTITADKSTSTAYMELSSLRSEDTAVYYC**ARGGTGFAY**WGQG |
| 21 | VH aa sequence of humanized variant of 4C11 | QVQLQQSGPGLVKPSQTLSLTCAIS**GYTFTSYN**MHWIRQPPGKGLEWIGA**IYPGNGDT**SYNQKFKGRVTITADKSTSTAYMELSSLRSEDTAVYYC**ARGGTGFAY**WGQG |
| 22 | VH aa sequence of humanized variant of 4C11 | QVQLQQSGPGLVKPSQTLSLTCAIS**GYTFTSYN**MHWVRQATGQGLEWMGA**IYPGNGDT**SYNQKFKGRLTISKDTSKNQVVLTMTNMDPVDTATYYC**ARGGTGFAY**WGQG |
| 23 | VH aa sequence of humanized variant of 4C11 | EVQLVQSGAEVKKPGESLRISCKGS**GYTFTSYN**MHWVRQATGQGLEWMGA**IYPGNGDT**SYNQKFKGRFTISRDDSKNTAYLQMNSLKTEDTAVYYC**ARGGTGFAY**WGQG |
| 24 | VH aa sequence of humanized variant of 4C11 | QVQLQESGPGLVKPSQTLSLTCTVS**GYTFTSYN**MHWVRQAPGQGLEWMGA**IYPGNGDT**SYNQKFKGRVTISVDTSKNQFSLKLSSVTAADTAVYYC**ARGGTGFAY**WGQG |
| 25 | VH aa sequence of humanized variant of 4C11 | QVQLVQSGAEVKKPGASVKVSCKAS**GYTFTSYN**MHWVRQATGQGLEWMGA**IYPGNGDT**SYNQKFKGRVTITADKSTSTAYMELSSLRSEDTAVYYC**ARGGTGFAY**WGQG |
| 26 | VH aa sequence of humanized variant of 4C11 | QVQLQQSGPGLVKPSQTLSLTCAIS**GYTFTSYN**MHWVRQATGQGLEWMGA**IYPGNGDT**SYNQKFKGRVTITADKSTSTAYMELSSLRSEDTAVYYC**ARGGTGFAY**WGQG |
| 27 | VH aa sequence of humanized variant of 4C11 | QVQLVQSGAEVKKPGASVKVSCKAS**GYTFTSYN**MHWVRQAPGQGLEWMGA**IYPGNGDT**SYAQKFKGRVTMTRDTSTSTVYMELSSLRSEDTAVYYC**ARGGTGFAY**WGQ |
| 28 | aa seq. of CDR1-H (Kabat) | SYNMH |
| 29 | aa seq. of CDR2-H (Kabat) | AIYPGNGDTSYNQKFKG |
| 30 | aa seq. of CDR3-H (Kabat) | GGTGFAY |
| 31 | aa seq. of CDR1-L (Kabat) | KASQSVSNDVA |

TABLE 1-continued

Description of the sequences:

| SEQ ID NO: | Description | Sequence |
|---|---|---|
| 32 | aa seq. of CDR2-L (Kabat) | YASNRYT |
| 33 | Forward primer | aaaagtactgcaagaaggactatgc |
| 34 | Reverse primer | ccctgcttatacacggagatg |
| 35 | Netrin-1 aa epitopic seq. | ARRCRFNMELYKLSGRKSGGVC |
| 36 | Netrin-1 epitopic cDNA seq. | GCCCGGCGCTGCCGCTTCAACATGGAGCTCTACAAGC TTTCGGGGCGCAAGAGCGGAGGTGTCTGC |

CDRs under IMGT are highlighted in bold in Table 1 where appropriate.

The present invention will now be described in further detail using examples that are to be considered as non-limiting embodiments.

EXAMPLE 1

Antibody Generation, Screen and Humanization

Figure 1:
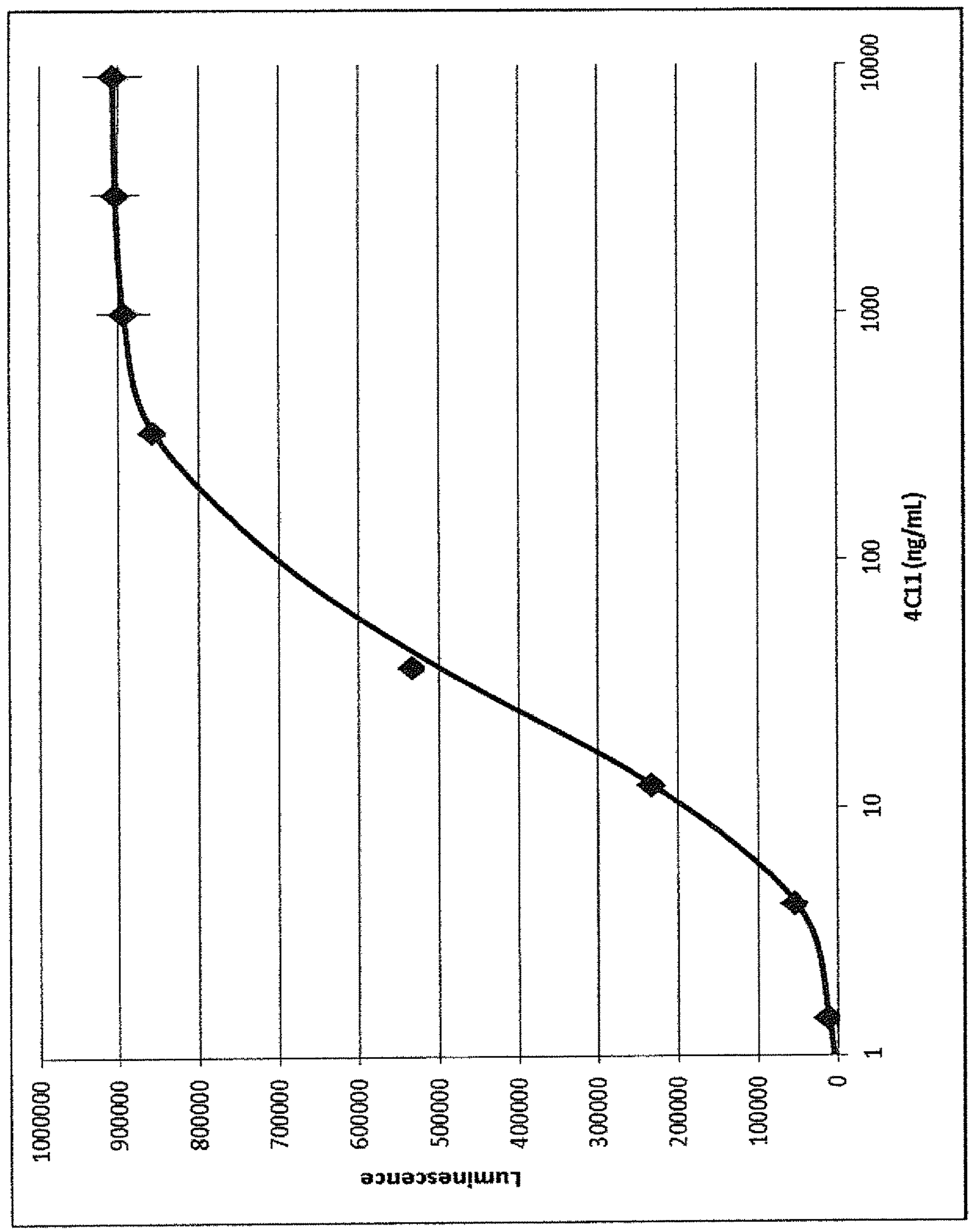
FIG. 1: ELISA binding assay of murine 4C11 to human Netrin-1. Various concentrations of 4C11 were incubated onto 96-well microtiter plate coated with FLAG®-tagged Netrin-1 (APOTECH). Bound 4C11 was detected using a goat anti-mouse IgG conjugated with horseradish peroxidase (Jackson Immunoresearch) and a chemiluminescent substrate (PIERCE ECL western blotting substrate). The luminescent was read on a Tecan Infinite F-500 luminometer.

HTP™ mice received 8 injections (everyday two days; first injection in presence of complete Freund adjuvant, the others with incomplete adjuvant) of 100 μg Netrin 1-Fc (Adipogen). Hybridoma fusion was performed 2 weeks after the first immunization (Abpro, Lexington, Mass.). Hybridoma supernatants were screened for specific monoclonal anti-Netrin 1 antibodies using a dual-antigen ELISA assay (Netrin 1-Fc and irrelevant Fc chimeric protein). A secondary ELISA-type assay was used to select monoclonal antibodies able to block the interaction of Netrin 1 with DCC or UNC5h2. A murine monoclonal antibody (murine 4C11 or NET1-M-mAb was then selected. This antibody is made of sequences SEQ ID NO: 12 and 13.

Humanization was performed as follows: double stranded DNA fragments coding for the light chain and heavy chain CDR sequences of murine 4C11 were combined with pools of human frameworks. Full length variable domains were then cloned into mammalian expression vectors. Light chain variable domains were cloned in frame with a secretion signal and a human kappa constant domain. Heavy chain variable domains were cloned in frame with a leader sequence and a human IgG1 constant domain. Diversity of the library and integrity of the LC and HC reading frames was checked by sequencing. Single clones were arrayed in 96 well format and plasmid DNA was prepped for transfection into CHO cells. The humanized library was transfected into CHO cells in 96 well format. Supernatants from transfected CHO cells were then collected at 48 hours post transfection and screened by Netrin-1 binding and competition ELISA assays. The light chain and heavy chain variable domains of the top 10 hits were sequenced, aligned, and analyzed. Humanized antibodies HUM01-10 as described above were generated.

EXAMPLE 2

MAb Production and Protein A Purification

Methods for producing monoclonal antibodies based on the nucleic acid sequences coding for the heavy and light chains are known from the person skilled in the art. Based on the sequences disclosed herein, the person skilled in the art may produce various murine, humanized and fully humanized antibodies directed against the linear epitope of SEQ ID NO: 3 or 35 or any variant thereof, such as the murine 4C11, and the humanized HUM1-10 and HUM1'-10' antibodies.

Mammalian cells are the preferred as hosts for production of therapeutic glycoproteins, due to their capability to glycosylate proteins in the most compatible form for human applications (Jenkins et al., *Nat Biotech.* 1996; 14:975-81). Mammalian host cells that could be used include, human Hela, 283, H9 and Jurkat cells, mouse NIH3T3 and C127 cells, Cos 1, Cos 7 and CV1 African green monkey cells, quail QC1-3 cells, mouse L cells and Chinese hamster ovary cells. Bacteria very rarely glycosylates proteins, and like other type of common hosts, such as yeasts, filamentous fungi, insect and plant cells yield glycosylation patterns associated with rapid clearance from the blood stream.

The Chinese hamster ovary (CHO) cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NSO- and SP2/0-mouse myeloma cells. Production from transgenic animals has also been tested (Jenkins et al., *Nat Biotech.* 1996; 14:975-81).

A typical mammalian expression vector contains the promoter element (early and late promoters from SV40, the long terminal repeats (LTRs) from Retroviruses e.g. RSV, HTLV1, HIV1 and the early promoter of the cytomegalovirus (mCMV, hCMV), which mediates the initiation of transcription of mRNA, the protein coding sequence, and signals required for the termination of transcription and polyadenylation of the transcript (BGH polyA, Herpes thimidine kinase gene of Herpes simplex virus polyA (TKpa), Late SV40 polyA and 3' UTR_Beta_Globin_polyA). Additional elements include enhancers (Eμ, hIE1), Kozak sequences, signal peptide and intervening sequences flanked by donor and acceptor sites for RNA splicing. Suitable expression vectors for use in practise in practising the present invention include, for examples, vectors such as pcDNA3.1, pcDNA3.3, pOptiVEC, pRSV, pEμMCMV, pMCMVHE-UTR-BG, pHCMVHE-UTR-BG, pMCMV-UTR-BG, pHCMV-UTR-BG, pMCMVHE-SV40, pHCMVHE-SV40, pMCMV-SV40, pHCMV-SV40, pMCMVHE-TK, pHCMVHE-TK, pMCMV-TK, pHCMV-TK, pMCMVHE-BGH, pHCMVHE-BGH, pMCMV-BGH, pHCMV-UTR-BGH).

The empty CHO Easy C cells are co-transfected with MAb expression vector for light and heavy chains following usual transient or stable transfection procedure. Secretion of H and L chains are enabled by the respective human IgH leader sequence. The coding regions for light and heavy chains are introduced into the MAb expression vector in the multiple cloning site. The transformants are analyzed for correct orientation and reading frame, the expression vector may be transfected into CHO cell line.

The harvested cell culture fluid produced from CHO cells is loaded onto the Hi Trap rProtein A column (GE Healthcare, Saint Cyr au Mont d'Or, France) that is equilibrated with Phosphate buffered saline, pH 7.2. The non-binding proteins are flowed through and removed by several washings with PBS buffer followed. The MAb is eluted off the Protein A column using a step of elution of 0.1 M citric acid at pH 3.0. Column eluent is monitored by A280. The MAb peak is pooled.

EXAMPLE 3

ELISA-Type Binding Assay OF 4C11 Antibodies to Netrin-1 (FIG. 1)

White 96-well microtiter plate (Costar 3912 Corning) was incubated overnight at 4° C. with 100 ng of His-tagged Netrin-1 (R&D 6419-N1) in 100 μL of Phosphate buffer saline (PBS). After three washings with 300 μL of PBS-0.05% TWEEN®-20 (PBS-T), the plate was blocked by addition of 100 μL of PBS-3% BSA and incubated 1 hour at room temperature. After three washings with 300 μL of PBS-T, the plate was incubated with various quantities (10 ng to 1200 ng) of the anti-netrin-1 antibody. After three washings with 300 μL of PBS-T, 100 μL of a relevant secondary antibody conjugated to horse radish peroxidase (e.g. goat anti-human IgG (Fc) Sigma A0170 or goat anti-mouse IgG light chain specific (kappa) Jackson Immunoresearch 115-035-174) diluted 1/10,000 in PBST-3% BSA was added and the plate was incubated 1 hour at room temperature. After three washings with 300 μL of PBS-T, 100 μL of a luminescent substrate of HRP (ECL western blotting substrate, PIERCE) is added. After 5 to 10 minutes, the luminescence was read on a Tecan Infinite F-500 luminometer.

FIG. 1 shows the typical dose-dependent interaction of the 4C11 murine antibody to adsorbed netrin-1 in the ELISA-type assay.

The concentration of the antibodies allowing 50% binding ($EC_{50}$) are calculated from the sigmoidal binding curves as displayed in FIG. 1. Table 1 displays the $EC_{50}$ values (in μg/mL and in nM) of the different murine (4C11 whole antibody as well as Fab and Fab'2 fragments) and humanized 4C11 antibodies.

TABLE 1

Potency of the various 4C11 variants to bind to netrin-1 (Example 3) or to impair the netrin-1 binding onto UNC5B (Example 5):

| | Potency Data | | | |
|---|---|---|---|---|
| | Binding (EC50) | | Ligand binding inhibition (IC50) | |
| | ng/mL | pM | ng/mL | pM |
| 4C11 murine IgG1 | 57 | 380 | 75 | 502 |
| 4C11 murine IgG2a | 63 | 420 | 85 | 567 |
| 4C11 Fab | 650 | 13000 | 844 | 16880 |
| 4C11 Fab'2 | 35 | 350 | 89 | 890 |
| HUM01 | 134 | 894 | 54 | 360 |
| HUM03 | 166 | 1107 | 65 | 434 |

TABLE 1-continued

Potency of the various 4C11 variants to bind to netrin-1 (Example 3) or to impair the netrin-1 binding onto UNC5B (Example 5):

| | Potency Data | | | |
|---|---|---|---|---|
| | Binding (EC50) | | Ligand binding inhibition (IC50) | |
| | ng/mL | pM | ng/mL | pM |
| HUM09 | 153 | 1021 | 71 | 474 |
| HUM08 | 134 | 894 | 77 | 514 |
| HUM06 | 139 | 927 | 82 | 547 |
| HUM05 | 151 | 1007 | 85 | 567 |
| HUM07 | 125 | 834 | 89 | 594 |
| HUM10 | 211 | 1407 | 110 | 734 |
| HUM04 | 198 | 1321 | 199 | 1327 |
| HUM02 | 260 | 1734 | 215 | 1434 |

HUM03 was selected for further experiments.
HUM03 may sometimes be called Humanized 4C11 hereafter.

EXAMPLE 4

Antibody Binding Assay by Surface Plasmon Resonance

The binding properties of the antibodies were analyzed using Biacore T I 00 (GE Healthcare) with the associated Software Biacore T100 Control Biacore TI 00 Evaluation, and the Chip:CM5-Chip as Assay format.

Murine 4C11 (IgG1) antibody (SEQ ID NO: 12 and 13) was captured via amine coupled capture molecules. A series with increasing concentrations of netrin-1 was injected. Chip surface with amine coupled capture molecule alone was used as reference control surface for correction of possible buffer-effects or non-specific binding of netrin-1.

Capture molecules: Anti-mouse IgG antibodies (from goat, Jackson Immuno Research).

Amine coupling of capture molecules. Standard amine coupling according to the manufacturer's instructions: running buffer: HBS-N buffer, activation by mixture of EDC/NHS, aim for ligand density of 10000 RU; the capture-antibodies were diluted in coupling buffer 10 mM NaAc, pH 4.5, c=30 μg/mL; finally remaining activated carboxyl groups were blocked by injection of 1 M ethanolamine.

4C11 antibody capture: Capturing of 4C11 antibody on flow cells 2 to 4: Flow 5 μL/min, contact time 72 seconds, c(Anti-mouse IgG antibodies)=5 nM. Capture buffer: PBS (pH7.4), 0.005% TWEEN ®20

Analyte sample: Classical concentration series were measured at a flow rate of 50 μL/min by consecutive injection of the analyte in 5 or 6 increasing concentrations (c=2-164 nM). Running buffer: 20 mM Hepes pH7.4, 600 mM NaCl, 0.005% Tween 20. The analyte was injected for 3 minutes followed by a dissociation phase of 90s.

Semi-quantitative surface plasmon resonance (SPR) analysis of Netrin-1 binding kinetics to captured 4C11 was performed using BIAcore analysis of binding of 4C11 murine antibody as provided and described in the present invention to human netrin-1. 4C11 antibody was captured on the chip surface via amine coupled anti-human IgG(Fc) molecules. A series with increasing concentrations of human netrin-1 was injected and the kinetic binding behaviour was monitored by SPR changes. Changes as relative units (RU) versus a control chip were recorded on the y-axis over time (x-axis). Representative association and dissociation curve of the captured analyte 4C11 at different concentrations of injected human netrin-1 was observed.

Kinetic parameters were then calculated by using the usual double referencing (control reference: binding of analyte to capture molecule; Flow Cell: netrin-1 concentration "0" as Blank) and calculation with model 'titration kinetics 1:1 binding.

Table 2 gives the affinitey data measured by SPR (BIACORE® T100) at 25°C in PBS:

| | Ka (M−1s−1) | Kd (s−1) | KD (nM) |
|---|---|---|---|
| Exp 1 | 1.4 × 105 | 1.8 × 105 | 13.3 |
| Exp 2 | 1.4 × 105 | 1.8 × 105 | 12.7 |

EXAMPLE 5

Figure 2:
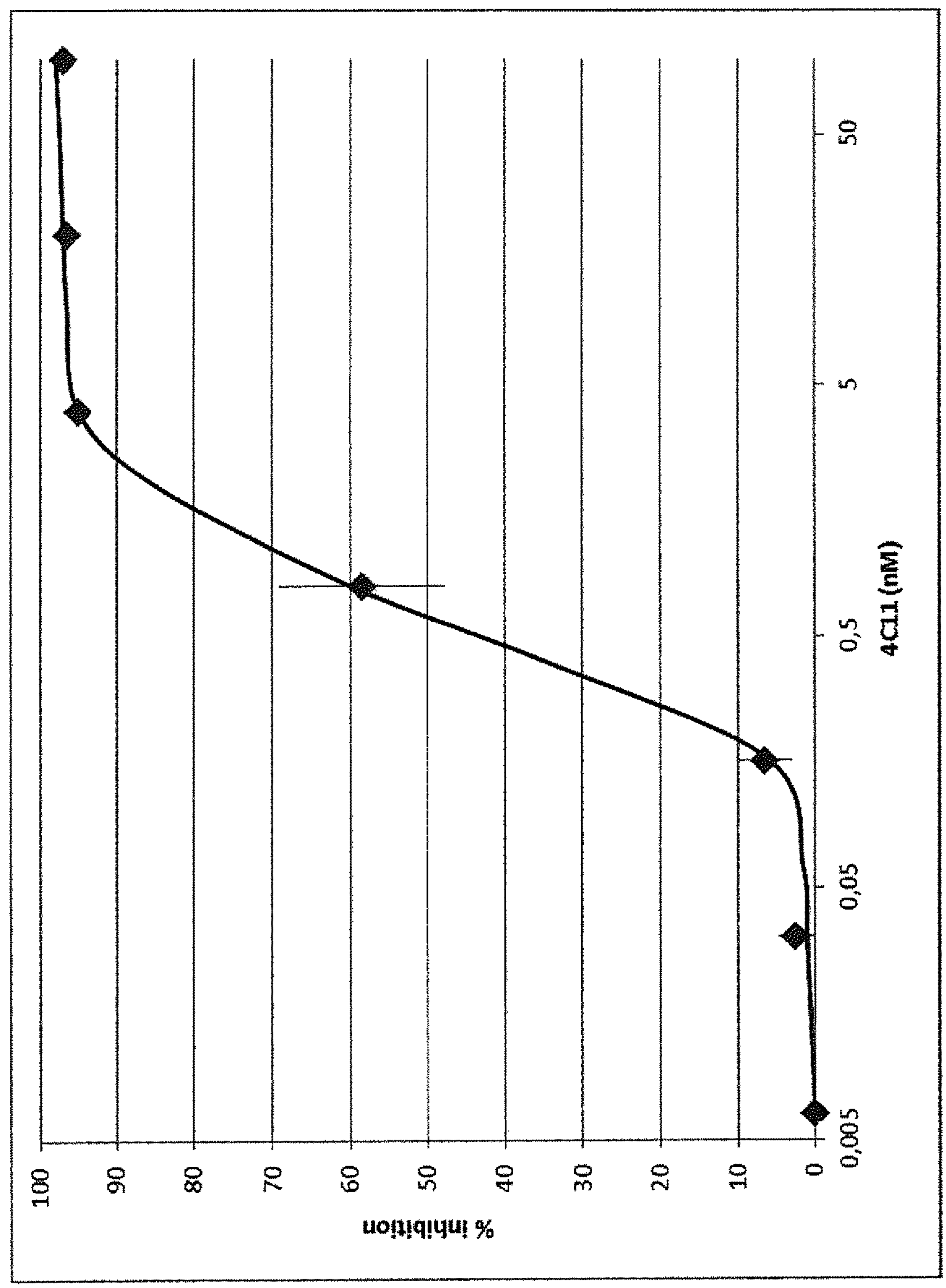
FIG. 2: Inhibition of Netrin-1 binding onto UNC5B-Fc by 4C11. FLAG®-tagged Netrin-1 (APOTECH) in presence of various concentrations of 4C11 were incubated onto 96-well microtiter plate coated with UNC5B-Fc (Netris). Bound Netrin-1 was detected using an anti-FLAG® antibody conjugated with horseradish peroxidase (Sigma) and a chemiluminescent substrate (PIERCE ECL western blotting substrate). The luminescence was read on a Tecan Infinite F-500 luminometer.

4C11 Inhibits the Binding of Netrin-1 TO UNC5B (FIG. 2)

White 96-well microtiter plate (Costar 3912 Corning) was incubated overnight at 4° C. with either 100 ng UNC5B-Fc (R&D 1006-UN-050) or DCC-Fc (R&D 844-DC-050) in 100 μL of Phosphate buffer saline (PBS). After three washings with 300 μL of PBS-0.05% TWEEN®-20 (PBS-T), the plate was blocked by addition of 100 μL of PBS-2% BSA and incubated 1 hour at room temperature. After three washings with 300 μL of PBS-T, the plate was incubated for 1 hour at room temperature, with 100 μL of PBS-1% BSA containing 50 ng/mL FLAG®-tagged netrin-1 (Adipogen) and various quantities (0,2 ng to 3000 ng) of the 4C11 antibody. After three washings with 300 μL of PBS-T, 100 μL of an anti-FLAG ®M2 monoclonal antibody conjugated to horse radish peroxidase (HRP) (Sigma A8592) diluted 1/5,000 in PBST-1% BSA was added and the plate was incubated 1 hour at room temperature. After three washings with 300 μL of PBS-T, 100 μL of a luminescent substrate of HRP (ECL western blotting substrate, PIERCE) is added. After 5 to 10 minutes, the luminescence was read on a Tecan Infinite F-500 luminometer.

FIG. 2 shows the typical dose-dependent inhibition of netrin-1 binding to UNC5B by increasing amounts of the murine 4C11 murine antibody in an ELISA-type assay.

Figure 5:
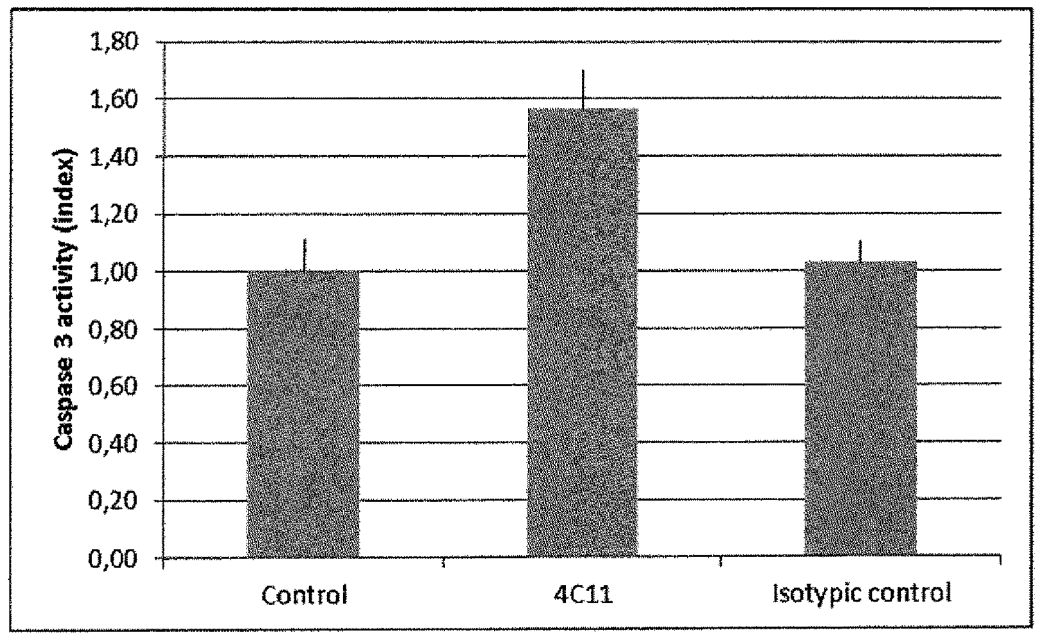
FIG. 5: Induction of caspase 3 in A549 adenocarcinomic human alveolar basal epithelial cells in presence of the murine 4C11 antibody.

The concentration of the antibodies allowing 50% inhibition ($IC_{50}$) are calculated from the sigmoidal binding curves as displayed in FIG. 5. Table 1 gives the $IC_{50}$ values (in μg/mL and in nM) of the different murine (4C11 whole antibody as well as Fab and Fab'2 fragments) and humanized 4C11 antibodies.

EXAMPLE 6

Figure 3:
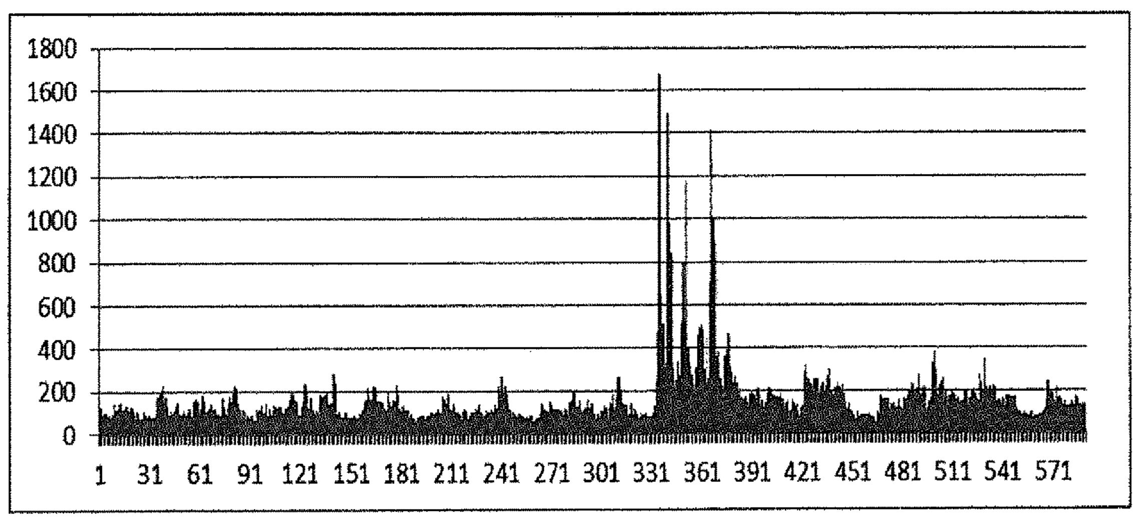
FIG. 3: Linear epitope mapping of 4C11 was performed using an array of 590 15-amino acid linear peptides covering the whole sequence of human Netrin-1 with a peptide-peptide overlap of 14 amino-acids. Binding of 4C11 on the peptide was revealed using a peroxidase (POD)-labeled anti-mouse IgG and a chemoluminescent substrate.
Figure 4:
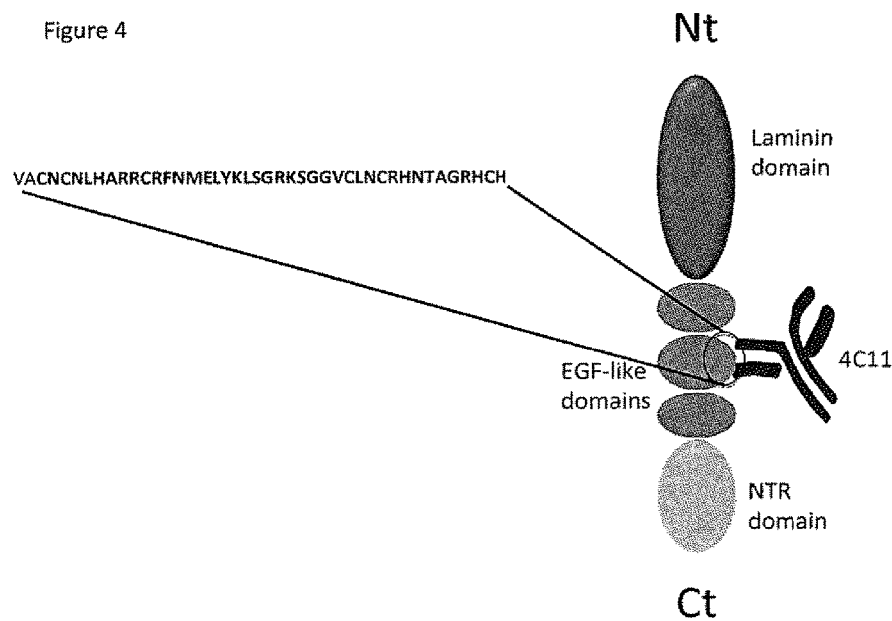
FIG. 4: Scheme showing the amino acid sequence of the Netrin-1 epitope (located in the second EGF-like laminin domain) SEQ ID NO: 3 recognized by the murine 4C11 antibody.

Netrin-1 Epitope Mapping of Murine 4C11 (FIGS. 3 AND 4)

Epitope mapping was performed using an array of 590 15-amino acid linear peptides covering the whole sequence of human Netrin-1 (without the signal peptide) with a peptide-peptide overlap of 14 amino acids. Linear peptides were synthesized using standard Fmoc-chemistry and deprotected using trifluoric acid. The 455-well credit-card format polypropylene cards containing the covalently linked peptides were incubated 30 min at 25° C. in PBST (PBS-1% TWEEN® 80) containing 5% SQ (SQ, Super-Q, 4% horse serum (v/v), 5% ovalbumin (w/v) in PBST. After washing, the peptides were incubated with the 4C11 (1 μg/mL) PBST-0.1% SQ. After washing, the peptides were incubated with a 1/1000 dilution of anti-mouse antibody peroxidase conjugate (SouthernBiotech) for one hour at 25° C. After washing, the peroxidase substrate 2,2'-azino-di-3-ethylbenzthiazoline sulfonate (ABTS) and 2 microliters of 3 percent H2O2 are added. After one hour, the color development are quantified with a charge coupled device (CCD)—camera and an image processing system.

FIG. 3 shows that the murine 4C11 interacts specifically with peptides included in the SEQ ID NO: 3: VACNCNLHARRCRFNMELYKLSGRKSGGVCLNCRHNTAGRHCH.

FIG. 4 is a cartoon displaying the location of the epitope recognized by the murine 4C11 antibody. This epitope is carried by the second EGF-like domain of Netrin-1.

Figure 9:
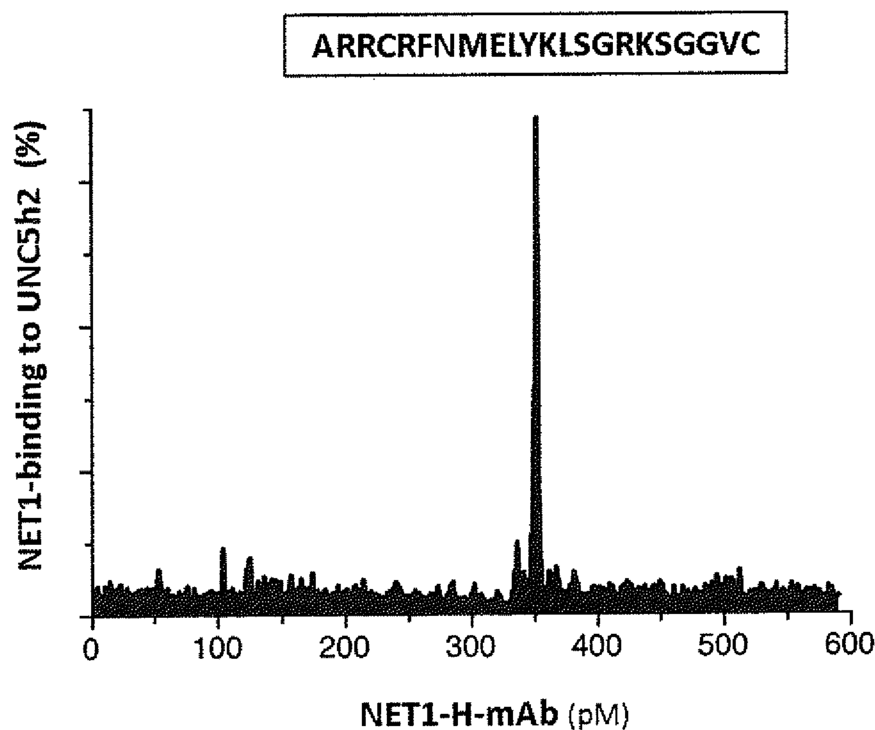
FIG. 9: Pepscan analysis of the NET1 binding domain of the anti-netrine 1 humanized 4C11 monoclonal antibody (NET1-H-mAb) HUM03. Raw Pepscan data obtained by screening humanized 4C11 mAb against the over-lapping peptide library of 590 linear peptides (x-axis). The signal strength of the interaction is visualized on the y-axis. The peak corresponds to the following amino-acid sequence: ARRCRFNMELYKLSGRKSGGVC (SEQ ID NO: 35).

Pepscan epitope mapping using the spot array of 590 15-amino acid linear peptides covering the whole sequence of human NET1. As shown in FIG. 9, the antibody HUM03 binds 8 overlapping peptides corresponding to the amino acid sequence “ARRCRFNMELYKLSGRKSGGVC” (SEQ ID NO: 35) which is present within the V-2 domain of NET1. The binding epitope of the antibody thus overlaps with the NET1 domain involved in the interaction with UNC5B. To confirm that the V-2 domain of NET1 is indeed responsible for the interaction with HUM03, we generated a collection of mutants and performed in vitro binding assays of these mutants with the antibody as well as with UNC5B. The point mutation K358L was sufficient to decrease interaction with the HUM03. The triple mutation R348A-R349A-R351A reduced the interaction.

EXAMPLE 7

4C11-Induced Caspase-3 In Human A549 Lung Adenocarcinoma Epithelial Cells (FIG. 5)

On day 1, cells were plated in serum free medium ($1.8\times10^5$ cells per well in six-well plates with 1 mL per well). On day 2, the medium was replaced with 1 mL fresh serum-free medium containing either vehicle (Ctrl), the mouse 4C11 antibody, or an murine IgG1,k irrelevant antibody (Ab) (10 μg/mL). Treatments were performed in duplicate. On day 3, cells from the 2 identically treated wells were harvested and combined as one pool. After centrifugation, cell pellets were resuspended in 55 μL of lysis buffer provided in the Caspase 3/CPP32 Fluorimetric Assay Kit (Gentaur Biovision, Brussels, Belgium). Apoptosis was then monitored by measuring caspase-3 activity using the above-mentioned kit. All values were normalized to the control.

FIG. 5 shows that the murine 4C11 antibody induces caspase 3 activity in human A549 lung adenocarcinoma epithelial cells.

EXAMPLE 8

Figure 6:
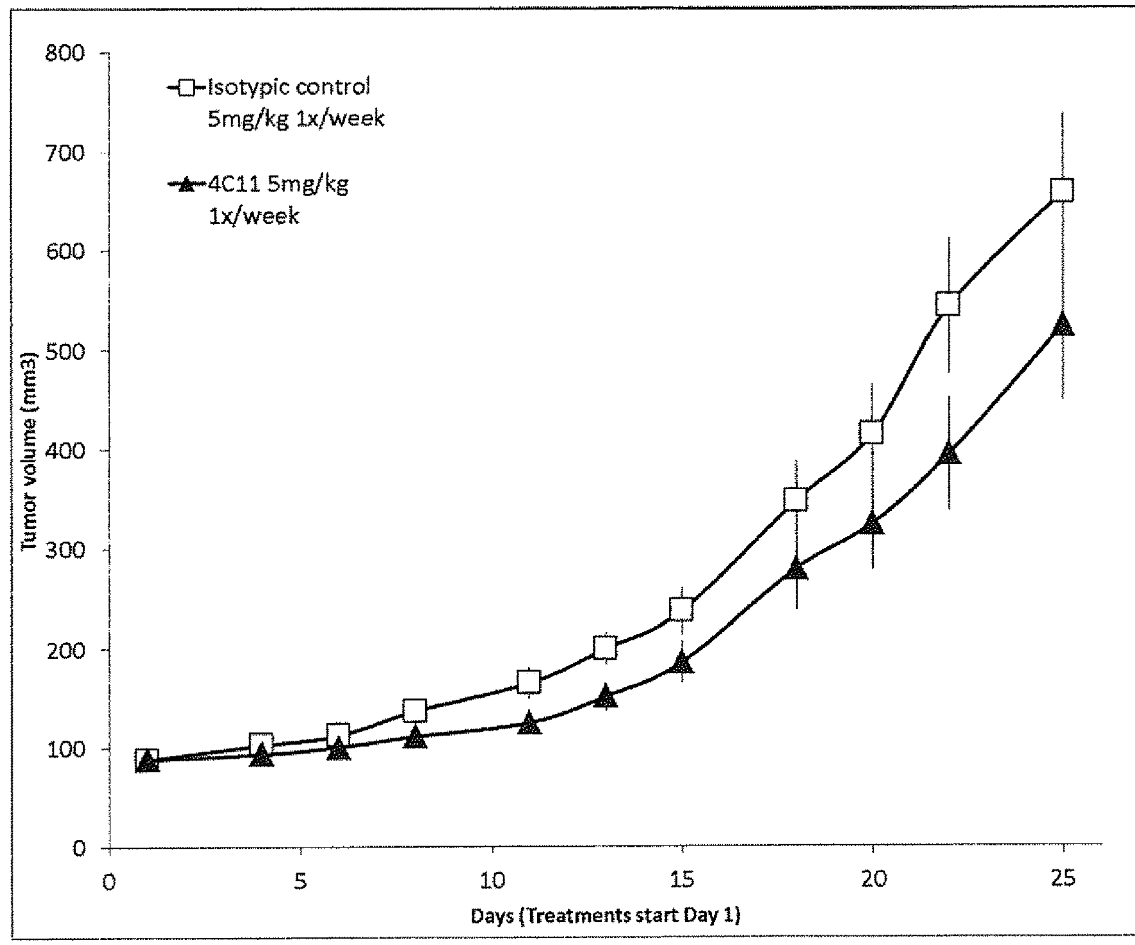
FIG. 6: Growth inhibition of human xenografts in nude mice treated with the murine 4C11 antibody. A549 human lung adenocarcinoma epithelial cells were injected subcutaneously to athymic (i.e. immunodeficient) nude mice. Once the tumor had reached approximately 100 $mm^3$, mice (n=10 per group) were treated intraperitoneally with 5 mg/kg once a week with 4C11 or an isotypic control (MOPC21).
Figure 7:
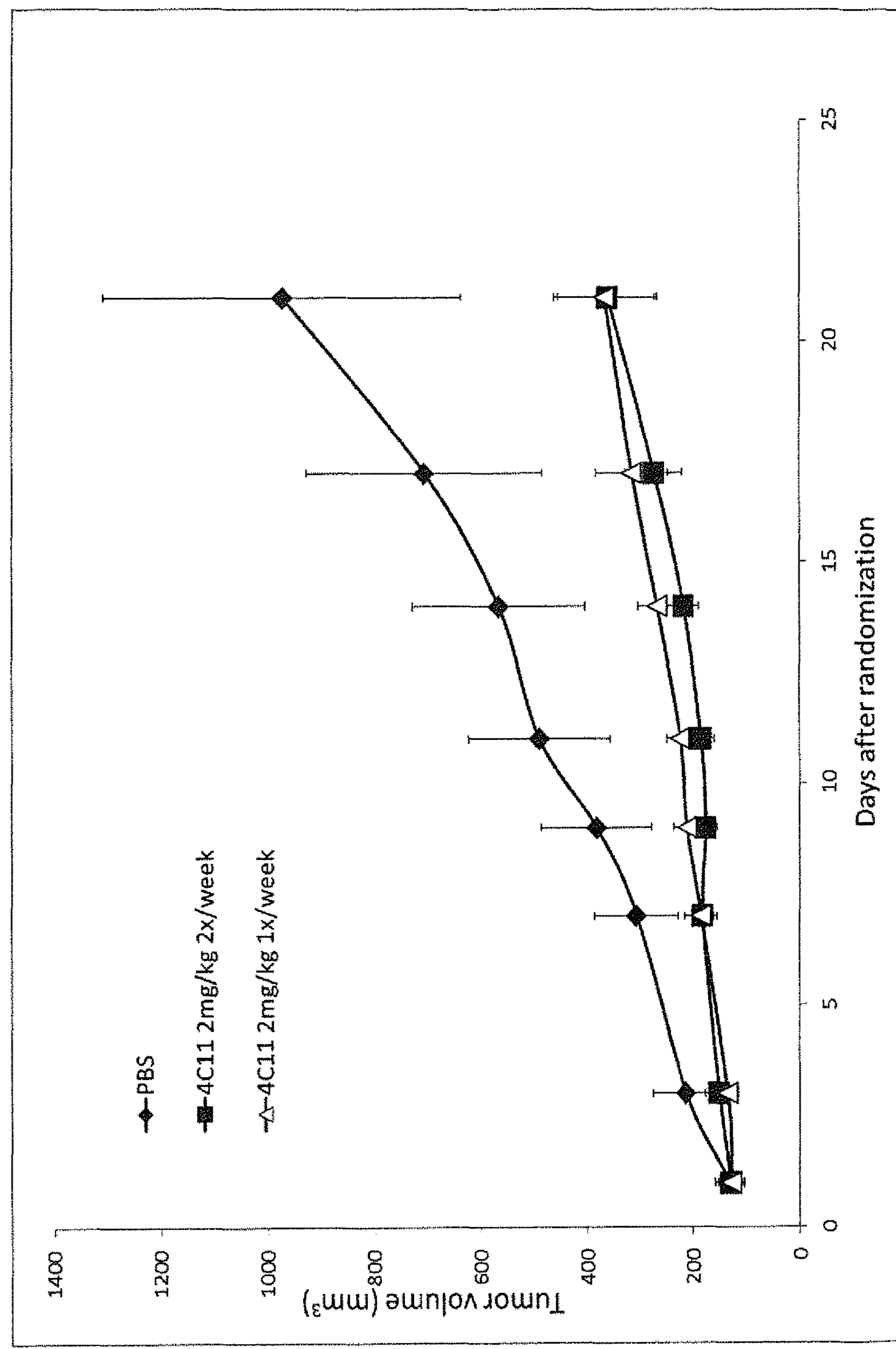
FIG. 7: Growth inhibition of human xenografts in nude mice treated with the murine 4C11 antibody. GRANTA-519 human mantle cell lymphoma cells were injected subcutaneously to athymic (i.e. immunodeficient) nude mice. Once the tumor had reached approximately 100 $mm^3$, mice (n=10 per group) were treated intraperitoneally with 2 mg/kg once a week or twice a week with 4C11 or with the vehicle (PBS).

In Vivo 4C11-Induced Tumor Growth Inhibition of A549 (Human Lung Adenocarcinoma Epithelial Cells) (FIG. 6) and GRANTA (Human Mantle Cell Lymphoma Cells) Cells Xenografts (FIG. 7)

Seven-week-old (20-22 g body weight) female athymic nu/nu mice were obtained from Charles River animal facility. The mice were housed in sterilized filter-topped cages and maintained in a pathogen-free animal facility. All tumors were implanted by s.c. injections of tumor cells ($10^7$ A549 cells or $10^6$ GRANTA cells) in 200 μL PBS into the right flank of the mice. Treatment with the 4C11 antibody started when tumors were established (V≈100 $mm^3$, approximately 15-20 days post-injection). Mice received intraperitoneal injection of the 4C11 antibody (various doses and schedules), the vehicle (PBS), or an isotypic control (MOPC21) (n=10 mice). Tumor sizes were measured with a caliper. Tumor volumes were calculated with the formula $v=0.5*(\text{length}*\text{width}^2)$.

Mice with A549 xenografts were treated with 5 mg/kg of 4C11 once a week, while mice with GRANTA xenografts received lower dose of 4C11 (2 mg/kg) once or twice a week.

FIGS. 6 and 7 demonstrated significant suppression of tumor growth of human A549 lung adenocarcinoma epithelial cells (A) and human GRANTA human mantle cell lymphoma (B) xenografted in immunodeficient mice.

The 4C11 antibody shows an inhibition of A549 and GRANTA tumor growth.

EXAMPLE 9

Figure 8:
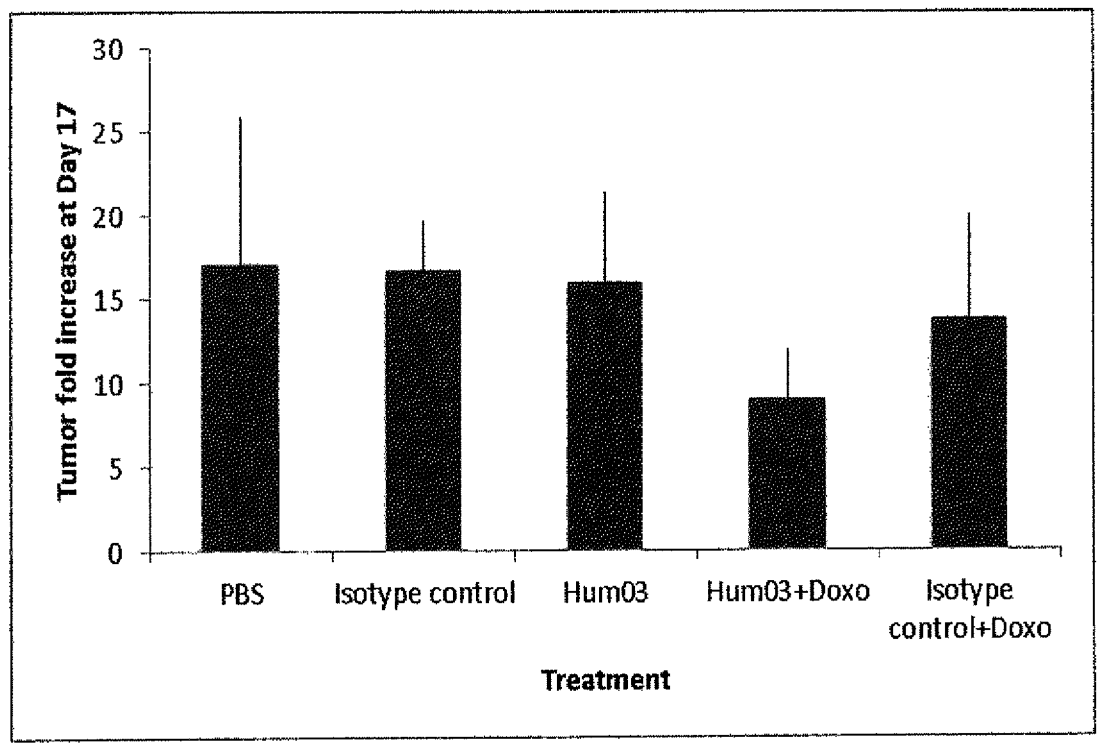
FIG. 8: In vivo effect of humanized 4C11 antibody (hum03) in the growth of rat transplantable osteosarcoma. Rat osteosarcoma tumors were transplanted in paratibial position after denudation of the periosteum (n=7). The rats were treated twice a week by intra-peritoneal injection of 4.4 mg/kg of humanized 4C11 hum03 or an isotypic control with or without doxorubicin (2 mg/kg) or with PBS. The figure displays the tumor fold increase at day 17.

Synergy Between Humanized 4C11 (hum03) and Doxorubicine In Rat Osteosarcoma (FIG. 8)

A radiation-induced rat osteosarcoma has been transformed into a transplantable model gratfed in paratibial position after denudation of the periosteum (ref. Allouche M. et al., 1980, *Int. J. Cancer* 26, 777-782). As no netrin-1 was expressed in this tumor, we stimulated netrin-1 and its receptors expression using a chemotherapy agent (Dox, Dorubicin) as recently published (cf Paradisi et al. 2013 *EMBO Mol Med* (2013) 5, 1821-1834). Rats grafted with the osteosarcoma received twice a week, intra-peritoneal injection of humanized 4C11 hum03 (4.4 mg/kg) or the vehicle (ctr). Some animals received in addition intra-peritoneal injection of doxorubicin (2 mg/kg). Tumor sizes were measured with a caliper. Tumor volumes were calculated with the formula $v=0.5*(\text{length}*\text{width}^2)$. In parallel, MRI is used to follow the growth pattern.

FIG. 8 shows that an inhibition of osteosarcoma growth is achieved in animals treated simultaneously with 4C11 and doxorubicin.

EXAMPLE 10

Effect of Murine 4C11 in Inflammatory Model of Spontaneous Colon Cancer Generated by Inflammation. (Mouse Model of IBD (Inflammatory Bowel Disease)-associated Colorectal Cancer)

(cf Ref *Proc Natl Acad Sci USA*. 2009 Oct. 6; 106(40): 17146-51).

Mice were treated with AOM+DSS and treated with PBS or 4C11 intraperitoneally 2 mg/kg twice a week (n=7) as described previously (Ref: Neufert C et al (2007) Nat Protoc 2: 1998-2004). Briefly, pathogen-free 8-week old female Wild-Type Balb/C mice were injected intraperitoneally with 10 mg/kg body weight of AOM dissolved in PBS. The day after, 2.5% DSS was given in the drinking water over one week, followed by 2 weeks of regular water. Mice were treated with DSS for 1 week every 2 weeks until the tenth week of the experiment and were injected three times per week with 4C11 or with PBS. The animals were sacrificed at the beginning of the tenth week and the colon was removed for histological analysis. Table 3 clearly shows that the treatment of the mice with the 4C11 antibody prevents or slow-down the development of inflammatory-driven colon adenocarcinomas.

Table 3: Effect of the anti-Netrin mAb 4C11 on inflammatory-driven colon tumors in vivo. Mouse model of IBD (Inflammatory Bowel Disease)-associated colorectal cancer was generated as already described (*Proc Natl Acad Sci USA*. 2009 Oct. 6; 106(40:17146-51). Mice were first treated with azoxymethane (AOM) and Dextran sulfate sodium (DSS) to induce colorectal cancer. Mice were treated with PBS or 4C11 intraperitoneally 2 mg/kg twice a week (n=7). Mice were sacrificed. The removed colon was fixed in formaldehyde for histological analysis. Table 3 presents the percentage of mice displaying various pre-cancerous or cancerous colon lesions.

| | Treatment | |
|---|---|---|
| Colon lesion | PBS | 4C11 |
| Focal hyperplasia | 0% | 86% |
| Low grade adenoma | 50% | 0% |
| High-grade adenoma | 16.7% | 0% |
| Early ADK | 33.3% | 42.8% |
| ADK | 66.7% | 14.3% |

EXAMPLE 11

Netrin-1 Protein Quantification in Human Cancer Cells

For immunoblot analysis, cells are lysed by sonication in modified RIPA buffer (50 mM Tris-HCl, pH7.5, 150 mM NaCl, 1% NP-40, 0.5% sodium deoxycholate, 0.1% SDS, 1 mM EDTA, protease inhibitor cocktail and 5 mM DTT) and incubated 1 h at 4° C. Cellular debris are pelletted by centrifugation (10.000 g 15' at 4° C.) and protein extracts (200 g per lane) are loaded onto 10% SDS-polyacrylamide gels and blotted onto PVDF sheets (Millipore Corporation, Billerica, Mass., U.S.A.). Filters are blocked with 10% non-fat dried milk and 5% BSA in PBS/0.1% TWEEN ® 20 (PBS-T) over-night and then incubated for 2 h with rabbit polyclonal α-netrin-1 (dilution 1:500, clone H104, Santa Cruz Biotechnology, Santa Cruz, Calif., USA) and mouse monoclonal β-actin (Santa Cruz Biotechnologies) antibodies. After three washes with PBS-T, filters are incubated with the appropriate HRP-conjugated secondary antibody (1:10000, Jackson ImmunoResearch, Suffolk, UK) for 1 h. Detection is performed using West Dura Chemiluminescence System (Pierce, Rockford, Ill., U.S.A.).

For immunofluorescence study, cells are detached, centrifuged on cover slips with a cytospiner (Shandon Cytospin 3, Thermo Scientific) and fixed for 30 minutes with 4% (v/v) paraformaldehyde. Cells are then permeabilized for 30 minutes in 0.2% TRITON® X-100/PBS and blocked in PBS containing 2% BSA and 2% normal donkey serum. Endogenous netrin-1 is stained using rat monoclonal α-netrin-1 antibody (R&D systems) and ALEXAFLUOR®-488 Donkey anti-rat IgG (Molecular probes). Nuclei are counterstained using Hoescht staining (Sigma).

EXAMPLE 12

Example of Cancers Over-expressing Netrin-1 and Expressing DCC and/or UNC5A and/or B and/or C and/or D to be Candidate for the Treatment With A UNC5-TRAP or Humanized 4C11 Antibody The percentage of netrin-1 overexpressing cases is given for each type of cancers for which expression of netrin-1 and its receptors have been quantified.

- 60% of metastatic breast cancer (Fitamant et al., PNAS 2008),
- 47% of non-small cell lung cancer (Delloye-Bourgeois et al., JNCI 2009),
- 38% of aggressive neuroblastoma (Delloye-Bourgeois et al., J. Exp. Med. 2009),
- 61% of pancreatic adenocarcinoma (Link et al., Annals of Chir. Onco. 2007; Dumartin et al., Gastro 2010),
- 100% of primary melanoma (n=7), melanoma metastasis (n=6) (Kaufmann et al., Cellular Oncology 2009),
- 76% of ovarian cancers (Panastasiou et al., Oncotarget 2011),
- 65% of glioblastoma,
- 60% of acute myeloid leukemia and chronic lymphocytic leukemia
- 50% of aggressive B-cell lymphoma,
- 30% of sarcoma,
- 40% of renal adenocarcinoma,
- 22% of head and neck cancers,
- Testicular cancers (36% of embryonal carcinoma, 50% of teratoma, 100% of yolk sac tumors)
- 50% of kidney cancers,
- 26% of stomach cancers,
- 19% of uterus cancers.

EXAMPLE 13

Quantitative RT-PCR Allowing to Assess Netrin-1 Expression or Overexpression in Accordance with PCT/EP2013/068937

Total RNA is extracted using NucleoSpin® RNA II Kit (Macherey Nagel, Düren, Germany) according to manufacturer's protocol. RT-PCR reactions are performed with iScript® cDNA Synthesis Kit (Biorad). One μg total RNA is reverse-transcribed using the following program: 25° C. for 5 min, 42° C. for 30 min and 85° C. for 5 min. For expression studies, the target transcripts are amplified in LightCycler® 2.0 apparatus (Roche Applied Science), using the LightCycler FastStart DNA Master SYBR Green I Kit (Roche Applied Science). Expression of target genes is normalized to glyceraldehyde 3-phosphate dehydrogenase (GAPDH) and phosphoglycerate kinase (PGK) genes, used as housekeeping genes. The amount of target transcripts, normalized to the housekeeping gene, is calculated using the comparative $C_T$ method. A validation experiment is performed, in order to demonstrate that efficiencies of target and housekeeping genes are approximately equal. The sequences of the primers are as follows:

```
                                   SEQ ID NO: 33
Forward primer: aaaagtactgcaagaaggactatgc.
                                   SEQ ID NO: 34
Reverse primer: ccctgcttatacacggagatg.
```

EXAMPLE 14

Netrin-1 Protein Quantification in Human Cancer Cells in Accordance with PCT/EP2013/068937

For immunoblot analysis, cells are lysed by sonication in modified RIPA buffer (50 mM Tris-HCl, pH7.5, 150 mM NaCl, 1% NP-40, 0.5% sodium deoxycholate, 0.1% SDS, 1 mM EDTA, protease inhibitor cocktail and 5 mM DTT) and incubated 1 h at 4° C. Cellular debris are pelletted by centrifugation (10.000 g 15' at 4° C.) and protein extracts (200 g per lane) are loaded onto 10% SDS-polyacrylamide gels and blotted onto PVDF sheets (Millipore Corporation, Billerica, Mass., U.S.A.). Filters are blocked with 10% non-fat dried milk and 5% BSA in PBS/0.1% tween® 20 (PBS-T) over-night and then incubated for 2 h with rabbit polyclonal α-netrin-1 (dilution 1:500, clone H104, Santa Cruz Biotechnology, Santa Cruz, Calif., USA) and mouse monoclonal β-actin (Santa Cruz Biotechnologies) antibodies. After three washes with PBS-T, filters are incubated with the appropriate HRP-conjugated secondary antibody (1:10000, Jackson ImmunoResearch, Suffolk, UK) for 1 h. Detection is performed using West Dura Chemiluminescence System (Pierce, Rockford, Ill., U.S.A.).

For immunofluorescence study, cells are detached, centrifuged on cover slips with a cytospiner (Shandon Cytospin 3, Thermo Scientific) and fixed for 30 minutes with 4% (v/v) paraformaldehyde. Cells are then permeabilized for 30 minutes in 0.2% TRITON® X-100/PBS and blocked in PBS containing 2% BSA and 2% normal donkey serum. Endogenous netrin-1 is stained using rat monoclonal α-netrin-1 antibody (R&D systems) and ALEXAFLUOR®-488 Donkey anti-rat IgG (Molecular probes). Nuclei are counterstained using Hoescht staining (Sigma).

EXAMPLE 15

In Vivo Xenograft Models

Different human cell lines (lung adenocarcinoma epithelial cell lines H358 and A549, and mantle cell lymphoma cell lines GRANTA-519 and diffuse large B-Cell lymphoma oci-ly3) in exponential growth were harvested from culture, washed twice with sterile PBS, counted and $5 \cdot 10^6$ cells were resuspended in PBS before s.c. implantation on the right flank of 5 week old female Swiss/nude mice. Tumor volumes (V) were determined by the formula V=0.5 (length× width$^2$) with a caliper. 100+/−20 mm$^3$ tumors were established before randomization into groups (10 mice each). Anti-netrine 1 antibody or an isotypic control were i.v. (H358, A549, oci-ly3) or i.p. (GRANTA-519) injected into mice at 10 mg/kg twice a week. Percent of Tumor Growth Inhibition (% TGI) was determined for each cell line grafted at the day (d) indicated in the following table and calculated by the formula TGI (%)=(1−T/C)×100 where T indicates the mean tumor volume of test group (treated with the anti-netrine 1 antibodies) at day d, and C indicates the mean volume of the isotype control-treated group. Tumor growth inhibition <50% is considered meaningful.

| Human cell line xenograft | Antibody | % TGI | Day d after treatment |
|---|---|---|---|
| GRANTA-519 | Murine 4C11 | 63 | 40 |
| H358 | Humanized 4C11 HUM03 | 56 | 40 |
| A549 | Humanized 4C11 HUM03 | 40 | 47 |
| OCYI3 | Humanized 4C11 HUM03 | 33 | 20 |

The murine and humanized antibodies of the invention had efficient tumor growth inhibiting effects.

The invention claimed is:

1. A netrin-1 binding monoclonal antibody or antigen-binding fragment thereof, wherein said antibody and said antigen-binding fragment thereof comprise:

(i) a variable heavy chain (VH) region comprising a CDR1-H polypeptide comprising SEQ ID NO: 28, a CDR2-H polypeptide comprising SEQ ID NO: 29 and a CDR3-H polypeptide comprising SEQ ID NO: 30; and (ii) a variable light chain (VL) region comprising a CDR1-L polypeptide comprising SEQ ID NO: 31, a CDR2-L polypeptide comprising SEQ ID NO: 32 and a CDR3-L polypeptide comprising SEQ ID NO: 9.

2. A pharmaceutical composition comprising the monoclonal antibody or antigen-binding fragment thereof according to claim 1, and a pharmaceutically acceptable vehicle, carrier or diluent.

3. The netrin-1 binding monoclonal antibody or antigen-binding fragment thereof according to claim 1, which comprises an amino acid sequence selected from the group consisting of SEQ ID NO: 10, SEQ ID NO: 11, SEQ ID NO: 12 and SEQ ID NO: 13.

4. The netrin-1 binding monoclonal antibody or antigen-binding fragment thereof according to claim 1, which comprises both sequences SEQ ID NO: 10 and 11.

5. The netrin-1 binding monoclonal antibody or antigen-binding fragment thereof according to claim 1, which comprises both sequences SEQ ID NO: 12 and 13.

6. The netrin-1 binding monoclonal antibody or antigen-binding fragment thereof according to claim 1, which comprises an amino acid sequence selected from the group consisting of SEQ ID NO:14-18 and 20-26.

7. The netrin-1 binding monoclonal antibody or antigen-binding fragment thereof according to claim 1, which comprises an amino acid sequence selected from the group consisting of SEQ ID NO: 14 to 18 and an amino acid sequence selected from the group consisting of SEQ ID NO: 20 to 26.

8. The netrin-1 binding monoclonal antibody or antigen-binding fragment thereof according to claim 1, which comprises a pair of amino acid sequences selected from the group consisting of pairs: SEQ ID NO: 14 and 20; 15 and 21; 16 and 22; 17 and 23; 17 and 24; 16 and 25; 17 and 26; 17 and 22; 18 and 25; and 16 and 21.

9. The netrin-1 binding monoclonal antibody or antigen-binding fragment thereof according to claim 1, which comprises a VL region comprising SEQ ID NO:16 and a VH region comprising SEQ ID NO:22.

10. The pharmaceutical composition of claim 2, wherein the monoclonal antibody or antigen-binding fragment thereof comprises the two amino acid sequences SEQ ID NO:16 and 22.

11. The netrin-1 binding monoclonal antibody or antigen-binding fragment thereof according to claim 1, which monoclonal antibody or antigen-binding fragment is humanized.

12. The netrin-1 binding monoclonal antibody according to claim 1, which comprises a VL region comprising SEQ ID NO: 16 and a VH region comprising SEQ ID NO: 22.

13. The netrin-1 binding monoclonal antibody of claim 1, having a light chain and a heavy chain and further comprising a human kappa constant domain in the light chain, and a human IgG1 constant domain in the heavy chain.

14. The netrin-1 binding monoclonal antibody of claim 12, having a light chain and a heavy chain and further comprising a human kappa constant domain in the light chain, and a human IgG1 constant domain in the heavy chain.

* * * * *